(12) United States Patent
Fields

(10) Patent No.: US 12,369,802 B2
(45) Date of Patent: *Jul. 29, 2025

(54) DEVICE FOR MAPPING A SENSOR'S BASELINE COORDINATE REFERENCE FRAMES TO ANATOMICAL LANDMARKS

(71) Applicant: Warsaw Orthopedic, Inc., Warsaw, IN (US)

(72) Inventor: Andrew Fields, Memphis, TN (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/335,218

(22) Filed: Jun. 15, 2023

(65) Prior Publication Data

US 2023/0337923 A1 Oct. 26, 2023

Related U.S. Application Data

(63) Continuation of application No. 16/850,284, filed on Apr. 16, 2020, now Pat. No. 11,717,173.

(51) Int. Cl.
*A61B 5/0205* (2006.01)
*A61B 5/11* (2006.01)
(Continued)

(52) U.S. Cl.
CPC .......... *A61B 5/0205* (2013.01); *A61B 5/1123* (2013.01); *A61B 90/39* (2016.02);
(Continued)

(58) Field of Classification Search
CPC ..... A61B 5/0205; A61B 5/1123; A61B 90/39; A61B 5/1126; A61B 5/4824; A61B 6/12;
(Continued)

(56) References Cited

U.S. PATENT DOCUMENTS 6,419,680 B1   7/2002  Cosman et al.
8,363,919 B2   1/2013  Sebok
(Continued)

FOREIGN PATENT DOCUMENTS

CN     103284743 B    3/2017
WO    2018139891 A1   8/2018
WO    2019055912 A1   3/2019

OTHER PUBLICATIONS

International Search Report and Written Opinion in Application No. PCT/US2021/021921 dated Jul. 1, 2021.

*Primary Examiner* — Anne M Kozak
*Assistant Examiner* — Kaitlyn E Sebastian
(74) *Attorney, Agent, or Firm* — FOX ROTHSCHILD LLP

(57) ABSTRACT

A coordinate locating device comprising a support structure removably connectable to a wearable sensor device being worn by an individual. The support structure comprising a planar surface. The device includes a plurality of different fiducial marker components connected to the planar surface. The plurality of different fiducial marker components includes a set of fiducial markers connected to the planar surface in a non-collinear configuration relative to each other to define a three-dimensional (3D) space of pixels in an image. The plurality of different fiducial marker components includes a distance calibration fiducial marker connected to the planar surface and being configured to define a distance calibration length of pixels in the image, the distance calibration fiducial marker being perpendicular to the planar surface and defining a calibration length to locate a point of origin of motion sensing by the wearable sensor device. A system and method are also provided.

13 Claims, 17 Drawing Sheets

(51) Int. Cl.
*A61B 5/316* (2021.01)
*A61B 90/00* (2016.01)
*A61B 5/00* (2006.01)
*A61B 6/00* (2006.01)
*A61B 6/12* (2006.01)
*A61B 6/50* (2024.01)

(52) U.S. Cl.
CPC ........... *A61B 5/1126* (2013.01); *A61B 5/4824* (2013.01); *A61B 6/12* (2013.01); *A61B 6/505* (2013.01); *A61B 6/5217* (2013.01); *A61B 2090/3966* (2016.02); *A61B 2090/3983* (2016.02)

(58) Field of Classification Search
CPC .................. A61B 6/505; A61B 6/5217; A61B 2090/3966; A61B 2090/3983; A61B 5/332; A61B 2017/00707; A61B 2017/00725; A61B 2034/2048; A61B 2034/2055; A61B 2090/3762; A61B 2090/3945; A61B 5/1114; A61B 5/1121; A61B 6/466; A61B 2560/0443; A61B 5/6833

See application file for complete search history.

(56) References Cited

U.S. PATENT DOCUMENTS

| | | | |
|---|---|---|---|
| 8,374,411 | B2 | 2/2013 | Ernst et al. |
| 9,220,573 | B2 | 12/2015 | Kendrick et al. |
| 9,232,928 | B2 | 1/2016 | Mostafavi |
| 9,610,056 | B2 | 4/2017 | Lavallee et al. |
| 9,987,092 | B2 | 6/2018 | Hladio et al. |
| 10,070,971 | B2 | 9/2018 | Palmatier et al. |
| 10,438,349 | B2 | 10/2019 | Yu et al. |
| 10,463,434 | B2 | 11/2019 | Siegler et al. |
| 2001/0031608 | A1 | 10/2001 | Dvir et al. |
| 2011/0275957 | A1 | 11/2011 | Bhandari |
| 2015/0170504 | A1* | 6/2015 | Jooste .................. A61B 5/6802 340/539.12 |
| 2017/0193706 | A1 | 7/2017 | Lo et al. |
| 2017/0273665 | A1 | 9/2017 | Kapoor et al. |
| 2018/0014888 | A1 | 1/2018 | Bonny et al. |
| 2018/0098715 | A1* | 4/2018 | Deitz .................. A61B 5/1071 |
| 2018/0153444 | A1 | 6/2018 | Yang et al. |
| 2019/0090955 | A1 | 3/2019 | Singh et al. |
| 2019/0201106 | A1* | 7/2019 | Siemionow ............... G06T 7/70 |
| 2019/0209080 | A1 | 7/2019 | Gullotti et al. |
| 2019/0236389 | A1* | 8/2019 | Obaidi .................. G06V 40/70 |
| 2019/0320995 | A1 | 10/2019 | Amiri |
| 2020/0046436 | A1 | 2/2020 | Tzeisler et al. |
| 2020/0257417 | A1 | 8/2020 | Kline et al. |
| 2020/0321121 | A1* | 10/2020 | Neumann ............... G06N 5/022 |

* cited by examiner

DEVICE FOR MAPPING A SENSOR'S BASELINE COORDINATE REFERENCE FRAMES TO ANATOMICAL LANDMARKS

CROSS-REFERENCE TO RELATED APPLICATIONS

This patent document claims priority to, and is a continuation of, U.S. patent application Ser. No. 16/850,284, filed on Apr. 16, 2020, titled "DEVICE FOR MAPPING A SENSOR'S BASELINE COORDINATE REFERENCE FRAMES TO ANATOMICAL LANDMARKS," the disclosure of which is fully incorporated into this document by reference.

FIELD

The present technology is generally related to devices for mapping a baseline coordinate reference frame of one or more sensors to one or more anatomical landmarks via ionizing radiation imaging.

BACKGROUND

Motion sensors attached to a patient can be used to assess many aspects of gait and posture. However, the motion sensor data can be difficult to associate with a suspected pain generator when the relationship between the sensor data and the patient's boney anatomy structures is unknown. Currently, the position of attached motion sensors with respect to musculoskeletal anatomy may be estimated using anthropometric relationships. However, estimating the position of motion sensors relative to the musculoskeletal using anthropometric relationships is imprecise.

Motion data is easy to collect and analyze, but it is collected from a device that sits outside of the subject's body. Motion data may provide insights about a person' gait, posture, balance, etc. However, motion data alone does not indicate which specific anatomical part of the body is actually moving as the motion data is collected.

SUMMARY

The techniques of this disclosure generally relate to a system, method and device that are configured to map a coordinate reference frame of one or more sensors embedded in a wearable sensor device to anatomical landmarks. The anatomic landmarks may include bones, joints, and organs such as without limitation a heart. In some embodiments, the system, method and devices correlates a suspected pain generator with motion sensed data.

In one aspect, the disclosure provides a coordinate locating device including a support structure removably connectable to a wearable sensor device being worn by an individual. The support structure includes a planar surface. The device includes a plurality of different fiducial marker components connected to the planar surface. The plurality of different fiducial marker components includes a set of fiducial markers connected to the planar surface in a non-collinear configuration relative to each other to define a three-dimensional (3D) space of pixels in an image. The plurality of different fiducial marker components includes a distance calibration fiducial marker connected to the planar surface and being configured to define a distance calibration length of pixels in the image. The distance calibration fiducial marker is perpendicular to the planar surface and provides a calibration to locate a point of origin of motion sensing by the wearable sensor device.

In another aspect, the disclosure includes a system comprising a wearable sensor device that includes an inertial measurement unit (IMU) and an ionizing radiation sensor. The ionizing radiation sensor is configured to, in response to sensing ionizing radiation, trigger a baseline timestamp to synchronize IMU data from the inertial measurement unit. The system includes a coordinate locating device that is configured to be removably attached to the wearable sensor device. The coordinate locating device includes a plurality of different fiducial marker components that is radiopaque to the ionizing radiation in a captured image.

In yet another aspect, the disclosure a method that includes sensing, by a wearable sensor device including an inertial measurement unit (IMU), inertial measurement data associated with an anatomical position of a boney anatomical structure. The method includes sensing, by an ionizing radiation sensor of the wearable sensor device, ionizing radiation to trigger a baseline timestamp to synchronize the inertial measurement data from the inertial measurement unit with an internal clock. The method includes imaging, using the ionizing radiation, a coordinate locating device attached to the wearable sensor device and including a plurality of different fiducial marker components being radiopaque to the ionizing radiation in a captured image.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
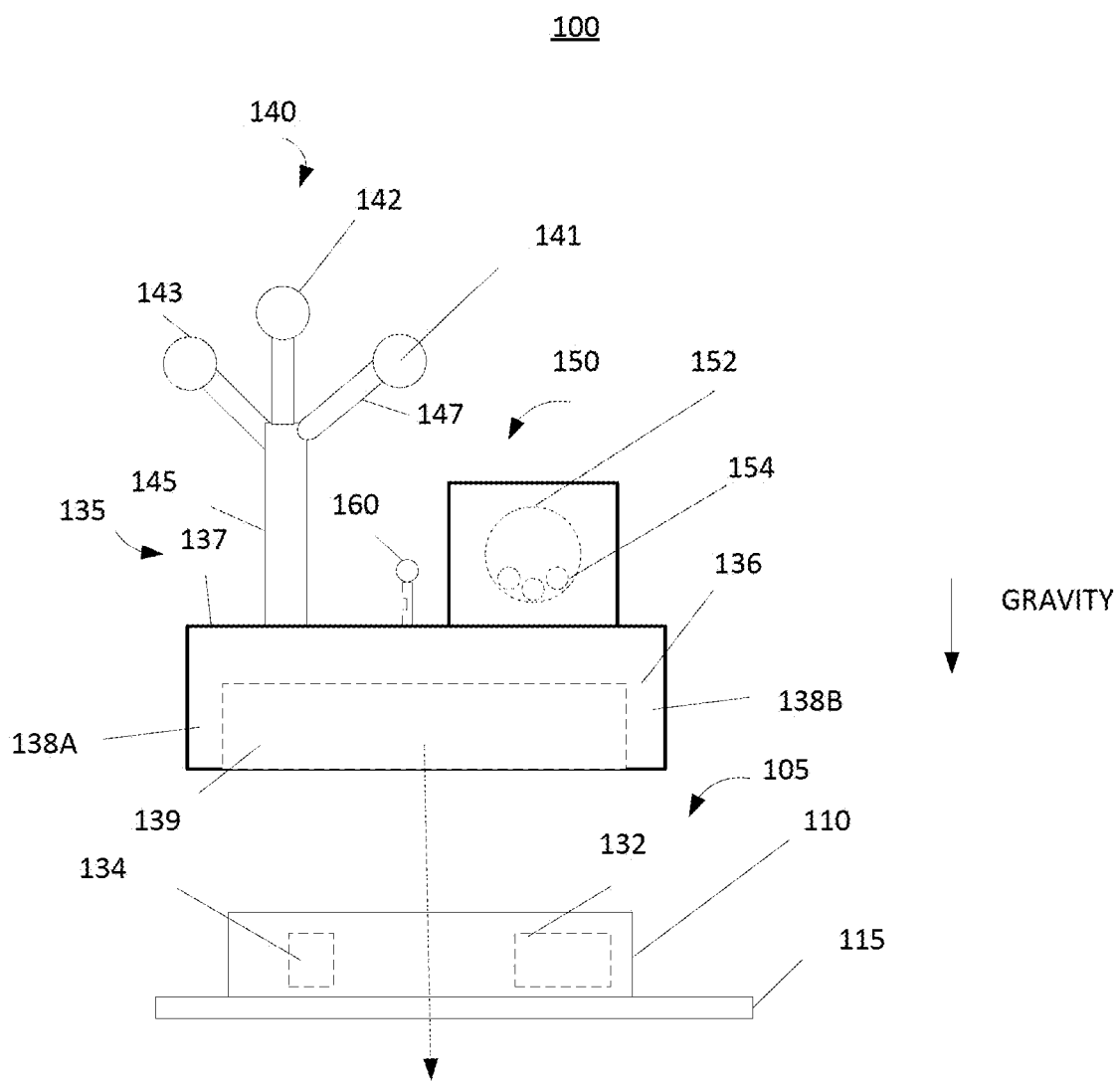
FIG. 1 is an exploded view of an embodiment of a motion sensor system.

The present invention may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other. Generally, similar spatial references of different aspects or components indicate similar spatial orientation and/or positioning, i.e., that each "first end" is situated on or directed towards the same end of the device. Further, the use of various spatial terminology herein should not be interpreted to limit the various location techniques or orientations for identifying objects or machines.

An "electronic device" or a "computing device" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, cameras, tablet computers, laptop computers, media players and the like. Electronic devices also may include appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion above, a client device, server device, virtual machine or container may be referred to simply as a "device" for brevity. Additional elements that may be included in electronic devices are discussed, for example, in the context of FIG. 5.

The terms "processor" and "processing device" refer to a hardware component of an electronic device that is configured to execute programming instructions. Except where specifically stated otherwise, the singular terms "processor" and "processing device" are intended to include both single-processing device embodiments and embodiments in which multiple processing devices together or collectively perform a process.

The terms "memory," "memory device," "data store," "data storage facility" and the like each refer to a tangible and non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

In this document, the term "imaging device" or "imaging machine" refers generally to one or more hardware sensors that are configured to acquire images, such as radiographic images. An imaging device may capture images, and optionally may be used for other imagery-related applications. For example, an imaging device can be an image camera, X-ray machine, computed tomography (CT) scan machine or other ionizing radiation imaging devices. The imaging device may be part of an image capturing system that includes other hardware and/or software components. For example, an imaging device can be mounted on an accessory or support structure. The imaging device can also be mounted to a wall, ceiling or other support. The imaging device may include a transceiver that can send captured digital images to, and receive commands from, other components of the system.

The disclosure provides a coordinate locating device having different radiographic fiducial marker components positioned a certain distance from one or more sensors located inside of a wearable motion sensor device being worn by a patient to generate a sensor's baseline coordinate reference frame when imaged. The sensor device may be configured to allow a patient to be imaged with ionizing radiation, for example, while wearing the sensor device. The resultant images can be used to determine the distance from the motion sensor of the sensor device to relevant boney anatomy structures.

FIG. 1 is an exploded view of an embodiment of a motion sensor system 100. The motion sensor system 100 may include a wearable sensor device 105 and a coordinate locating device 135 removably coupled to the wearable sensor device 105. The wearable sensor device 105 may include a housing 110 configured to be attached to a wearer, such as a wearer's trunk or back.

Figure 2A:
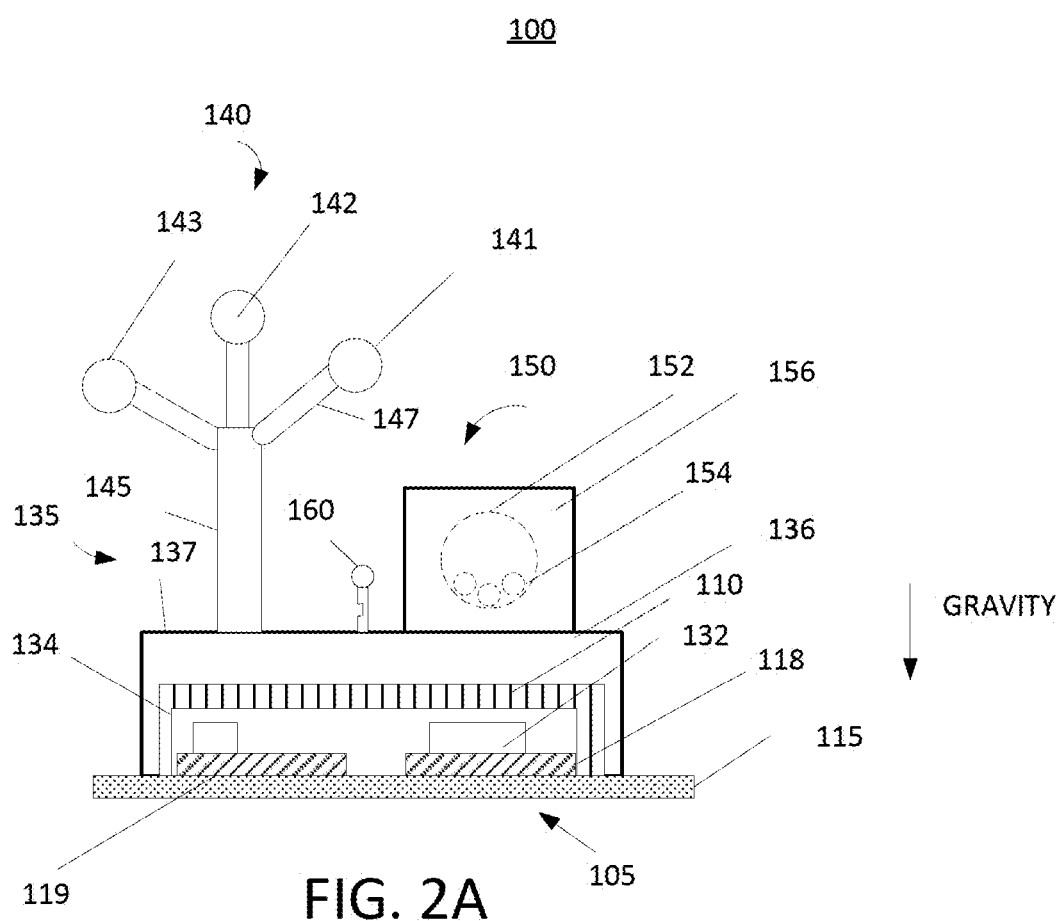
FIG. 2A is a side view of the motion sensor system of FIG. 1 with an embodiment of a housing of a wearable sensor device shown the cross-section, the gravity indicator shown in phantom and the coordinate locating device installed.
Figure 2B:
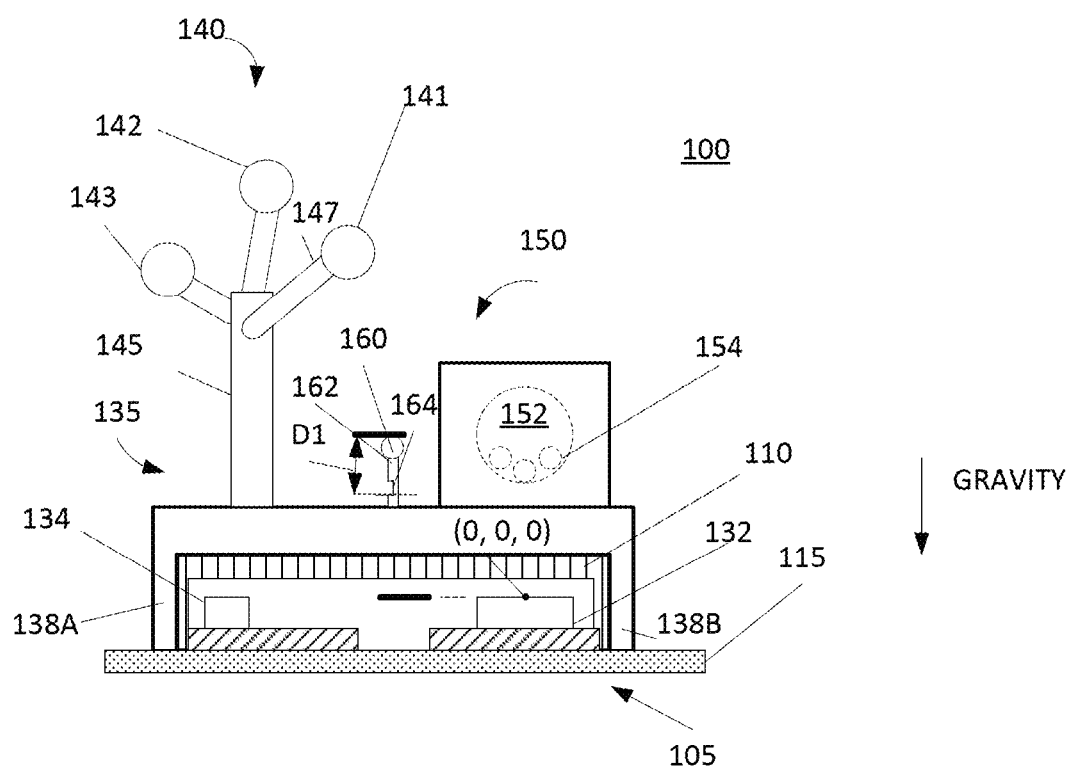
FIG. 2B is a side view of the motion sensor system of FIG. 2A with a distance calibration phantom and the point of sensing origin indicated.
Figure 2C:
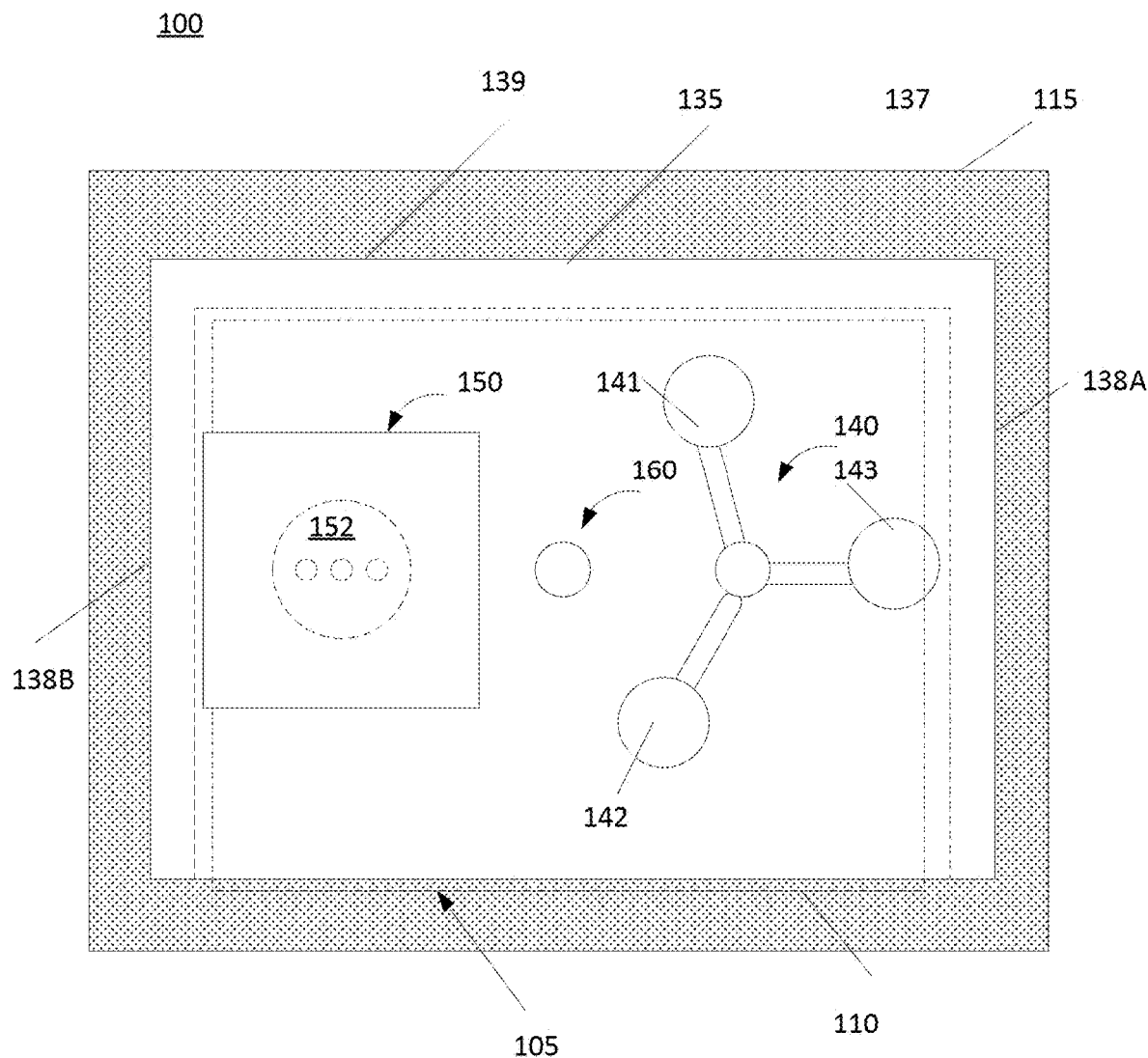
FIG. 2C is a top view of the motion sensor system of FIG. 1.
Figure 3:
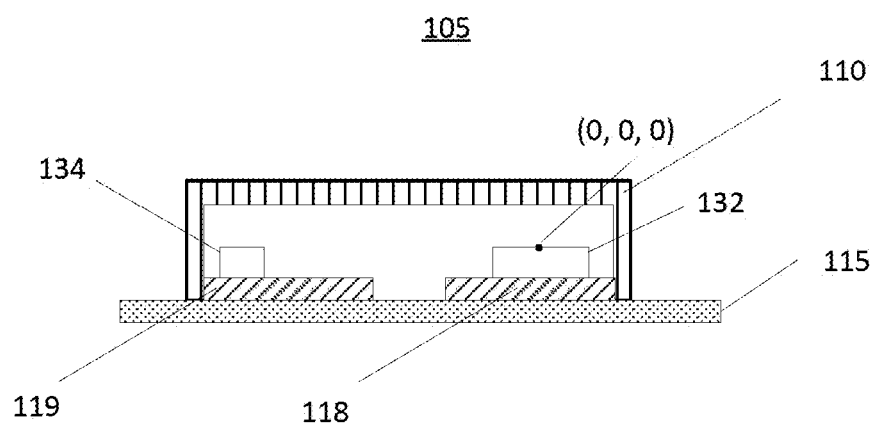
FIG. 3 is a side view of an embodiment of the wearable sensor device with the housing shown in cross-section.
Figure 4:
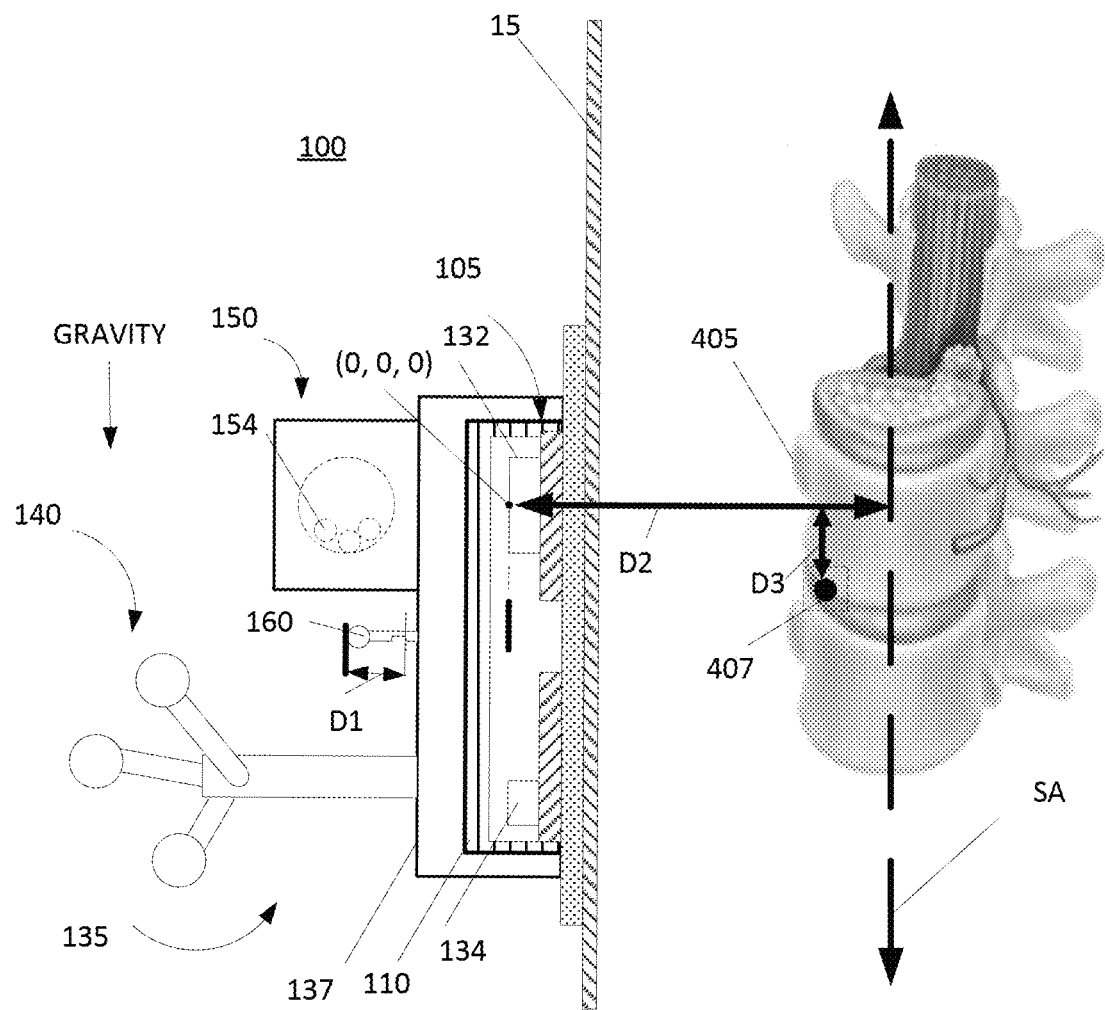
FIG. 4 is a diagram of an example of the motion sensor system attached to a patient being imaged, the housing of the wearable sensor device shown in cross-section.

The system 100 of FIG. 1 will be described also in relation to FIGS. 2A-2C and 3-4. FIG. 2A is a side view of an embodiment of the motion sensor system 100 of FIG. 1 with the housing 110 of a wearable sensor device 105 shown in cross-section, a gravity indicator, denoted by the reference numeral 150, shown in phantom and the coordinate locating device 135 installed. FIG. 2B is a side view of an embodiment of the motion sensor system 100 of FIG. 2A with a distance calibration phantom and the point of sensing origin (e.g., point denoted by 0, 0, 0) indicated. FIG. 2C is a top view of an embodiment of the motion sensor system of FIG. 1. FIG. 3 is a side view of an embodiment of the wearable sensor device 105 with the housing shown in cross-section. FIG. 4 is a diagram of an embodiment of the system 100 attached to a patient being imaged by imaging machine 410, the housing of the wearable sensor device 105 shown in cross-section. The point of sensing origin may be located to define the point of motion sensing that corresponds to a center of sensing by the IMU 132. The wearable sensor device 105 may not be movable (i.e., remains stationary) with respect to the boney anatomy landmark after the imaging measurements are taken.

The coordinate locating device 135 may include a support structure 136 removably connectable to a wearable sensor device 105, the support structure 136 may include a planar surface 137. The coordinate locating device 135 may include different fiducial marker components 140, 150 and 160 that may be connected to the planar surface 137 of the support structure 136. By way of non-limiting example, a first fiducial marker component may include a set of fiducial markers 141, 142, 143 connected to the planar surface 137 in a non-collinear configuration relative to each other to define or locate a three-dimensional (3D) space of pixels in an image. The set of fiducial markers may include three fiducial markers positioned at certain distances relative to each other and at certain angles to define a 3D space of pixels in an image. Additional and/or alternate number of fiducial markers may be used within the scope of this disclosure.

Each different fiducial marker component 140, 150 and 160 provides different coordinate location parameters. For example, the first fiducial marker component 140 may provide a three-dimensional location and orientation parameter. A second fiducial marker component may provide the direction of the gravity vector. A third fiducial marker component 160 may locate a point of sensing origin of the motion sensor of the wearable sensor device 105.

In the illustrations, a set of three markers are shown including a first maker 141, a second marker 142 and a third marker 143. There are three arms, one for each marker. Some portion of the markers 141, 142 and 143 may be arranged in 3D space via the known configuration of the marker support structure 145 so that when analyzing the images using image processing, the computing system knows the orientation and location of the device 105 from a two-dimensional (2D) image. The marker support structure 145 may include marker support arms 147 with each arm supporting a respective one fiducial marker of the marker set (i.e., first fiducial marker component 140). The fiducial markers 141, 142 and 143 are is shown as radiopaque ball-shaped elements. However, other geometric shapes, such as a three-dimensional shaped square, triangle, rectangle, or other shape, may be used.

The third fiducial marker component 160 may include a distance locator fiducial marker, denoted by the reference numeral 160, connected to the planar surface 137 that may be configured to define a distance calibration phantom length D1 of pixels in an image. The distance location fiducial marker 160 may be perpendicular to the planar surface 137. The distance locator fiducial marker 160 may include a stem 162 having a stem length. The stem may include a first end connected to the planar surface 137. The distance locator fiducial marker 160 may include a radiopaque marker connected to a second end of the stem 162, the radiopaque fiducial marker 160 has at least one dimension. For example, the radiopaque fiducial marker 160 may have a geometric shape with a dimension that extends the length of the stem. The distance locator fiducial marker 160 may include a notch 164 formed in the stem 162 where the distance calibration phantom length D1 is measured from a location associated with the notch 164 to a location of the radiopaque fiducial marker 160. In the illustration, the location is the furthest end of the radiopaque marker.

The fiducial marker 160 is shown as a radiopaque ball-shaped element. However, other geometric shapes, such as a three-dimensional shaped square, triangle, rectangle, or other shape, may be used.

The second fiducial marker component 150 may include at least one gravity direction fiducial marker 154, shown in phantom. The at least one gravity direction fiducial marker 154 is responsive to a force of gravity such that the force of gravity moves the at least one gravity direction fiducial marker 154 to indicate a direction of gravity vector at an instantiation of imaging at which the image is captured. The support structure 136 may further include a chamber 152, show in phantom, mounted to the planar surface 137. The at least one gravity direction fiducial marker 154 may include a plurality of loose radiopaque balls configured to move within the chamber 152 in response to the force of gravity. By way of non-limiting example, the chamber 152 is formed in a housing 156 where the housing 156 is mounted to the planar surface 137. In another scenario, the chamber 152 may be fluid filled with at least one gravity direction fiducial marker being a floatation element. The gravity direction fiducial marker 154 is captured in an image to show the direction of the gravity vector when the patient is at rest, such as during imaging of the patient.

The different fiducial marker components may be fabricated from metal, plastic or other composite material that is radiopaque in response to ionizing radiation. In some embodiments, each fiducial marker of a different function may have a different level of radiopacity, in response to the ionizing radiation of the imaging machine 410 so that the different functional elements of the marker components can be distinguished. In other scenarios, the fiducial maker of a different function may have a different geometric shape for distinguishing the different markers. Some fiducial markers may be passive markers while some are active markers (i.e., light emitting diode).

The different coordinate locating functions by the coordinate locating device will be described in more detail in relation to FIGS. 9A-9B and 10-12. The support structure 136 may include side walls 138A and 138B that may be parallel to each other and perpendicular to the planar surface 137. The distance between the first and second side walls 138A and 138B allows the housing 110 of the wearable sensor device 105 to fit therebetween. The support structure 136 may include a third side wall 139 perpendicular to and extend between the side walls 138A and 138B. The support structure 136 may include three walls with one side open to slide the housing 110 between the side walls 138A and 138B. When the patient is standing, for example, the third side wall 139 may prevent the coordinate locating device from sliding off of the housing 110 of the wearable sensor device 105. The housing 110 will have known dimensions relative to the support structure 136 of the coordinate locating device 135.

The housing 110 may include a skin-contacting interface 115. In FIGS. 2A-2C and 3, the skin-contacting interface 115 is shown with dotted hatching. The skin-contacting interface 115 may include an adhesive compatible with attachment to skin 15 (FIG. 4). The housing 110 is shown in vertical line hatching.

The system 100 may include an inertial measurement unit (IMU) 132. The wearable sensor device 105 may be designed to be worn for one or more days by patients experiencing musculoskeletal pain and/or neurological symptoms. Similar to a Holter monitor, the wearable sensor device 105 may continuously collect data about a patient's condition while they go about their daily life. Instead of measuring heart activity through surface electrodes as is done with a Holter monitor, the wearable device 105 may use the IMU 132 to measure the motion patterns of the region of the body to which it is adhered. These motion patterns may be used to monitor musculoskeletal and/or neurological conditions and to measure the impact that the disease is having on the everyday life of the wearer (i.e., patient).

The system 100 may include an ionizing radiation sensor 134. The ionizing radiation sensor 134 may be an X-ray sensitive element. The device 105 may include a circuit board 118 with an IMU 132 electrically coupled thereto. The device 105 may include circuit board 119 with an ionizing radiation sensor 134 electrically coupled thereto. The circuit board 118 and circuit board 119 are represented in diagonal hatching. While, the illustration illustrates two separate circuit boards, the circuit boards may be circuit board portions of a single circuit board in some scenarios.

The ionizing radiation sensor 134 may be an X-ray sensitive element. It may provide a timestamp associated with the time of the detection of the X-ray so that the sensor data could be "synchronized" with the X-ray(s). In other words, the instantiation in time at which an image is captured for a baseline coordinate reference is synchronized to the trigger generated by the ionizing radiation sensor 134, as will be described in more detail in relation to FIG. 5.

The sensor device 105 via the skin-contacting interface 115 may be applied to the back, such as the upper back, lower back or middle back, of a patient where it may remain for multiple days, actively recording sensed data. By way of non-limiting example, the sensor device 105 is configured to monitor the motion of the torso-specifically the flexion, extension, lateral bending, and axial rotation allowed by the hips and lumbar spine. The relationship between the motion of the torso recorded by the wearable device 105 and the underlying boney anatomy may be determined with a secondary source of data (e.g., imaging machine 410).

The coordinate locating device 135 may be used to reveal a baseline relationship between the motion of the torso and the positions of the bones and joints of the lumbo-pelvic-hip complex. The embodiments herein may be used to determine the distance between a motion sensor and a joint. For example, the embodiments may place the wearable sensor device 105 on a forearm, an elbow and/or shoulder. The wearable sensor device 105 may be head-mounted, neck mounted or face mounted by the jaw. The wearable sensor device 105 may be mounted on the cervical spine or other portion of the spine. The wearable sensor device 105 may be mounted on the leg, such as near a hip joint, a knee joint or ankle joint. The coordinate locating device 135 may then be used to reveal a baseline relationship between the bones and joints.

The wearable sensor device 105 may be configured to provide a surgeon/radiologist with important context for interpreting an image captured using an X-ray machine or CT scan machine. For example, standing X-rays are often used to determine the amount of angular correction required in a spine surgery. It is assumed that the posture of the individual in the X-ray is representative of that individual's "natural" posture. The wearable device 105 provides sensed data to confirm the "natural" posture of the patient because it collects multiple days of posture data. During an initial image(s), baseline information is captured that can be later compared with the sensed data during a monitoring period.

One or more artificial intelligence (AI) algorithms, such as machine learning algorithm (ML) or deep learning neural network (DL) may be used to determine the patient's natural standing posture by analyzing his or her standing posture during their daily life. Multiple algorithms may be used in succession or a staged approach to analysis. In one embodiment, the first stage of the analysis could be a series of ML or DL algorithms to identify the time(s) within the data that the wearer was standing. A second stage could then analyze the data identified as standing and provide an assessment of the most common postures. The most common postures could be analyzed together to generate a summary "natural" posture.

The wearable sensor device 105 may include other sensors (not shown) mounted to a circuit board. Other sensors may include, without limitation, electrocardiogram (ECG) sensors, electromyography (EMG) sensors, barometers, thermometers or other thermal sensors, microphones, photoplethysmography (PPG) and/or the like. For example, the data produced by an ECG sensor is highly dependent on where the surface electrodes are placed. If the surface electrodes are placed close to the heart and oriented to align with the mean electrical vector produced by the depolarizations of the heart chambers, then the ECG waveform is optimal. If the electrodes are moved away from the heart or misaligned with the mean electrical vector, then the ECG waveform changes. It would be beneficial to be able to predict a change in the ECG waveform by knowing the position of the ECG electrodes on the chest through the method described in this patent. In some embodiments, the coordinate locating device 135 may be configured to adapt to other sensors or electrodes such as those for ECG sensors.

The system 100 may be configured to map the coordinate reference frame of one or more sensors embedded in the wearable sensor device 105 to anatomical landmarks. The anatomic landmarks may include bones, joints, and organs such as without limitation a heart. The device may map accelerometer coordinate reference frame, as well as a gyroscope and magnetometer. The sensor coordinate reference frame(s) may be fixed. There is one coordinate reference frame per sensor. The sensor's coordinate reference frame may cover all anatomic landmarks.

Referring now to FIG. 4, the coordinate locating device 135 may include a distance locator 160 that defines or locates a distance calibration phantom length D1 of pixels in an image. Assume that for the sake of discussion, the view in FIG. 4 is a patient standing for a sagittal (longitudinal) X-ray. This can be applicable to a coronal plane CT scan, as well. A distance may be calculated to important radiographic landmarks and fiducial marker components. The device 105 uses the distance from the sensing center of the IMU 132 to the point of known distance (POKD) where a pixel/distance ratio is calculated. Then, the ratio is applied to calculate the distance to a boney anatomy landmark of interest. The POKD in the illustration corresponds to the distance locator 160. The distance locator 160 may be used interchangeably with the terms "third fiducial marker component," "point of known distance" and "fiducial marker."

Phantom is an accepted term for an item that is used as a reference in radiography. The most common use of a "phantom" can be used to estimate bone density in radiography. The phantom has different regions of known density/radiopacity and it is placed next to the bone being studied. The greyscale color of the bone is then compared to the greyscale color of the regions of the phantom. The region of the phantom that matches the color of the bone tells you the approximate density of the bone.

The position and orientation of a patient's anatomy structures 405 may be determined using a vision system employing ionizing radiation to capture both the radiopaque markers and the boney anatomy structures 405 correlated with IMU data from an IMU affixed to the patient's skin 15 at the instantiation of imaging. The location of the anatomy landmark 407 may be located in the image. The location of the anatomy landmark 407 may be registered by determining distances D2 and D3 relative to the spine's axis SA where boney anatomy structures rotate or bend relative to the spine's axis SA. The distance D2 is orthogonal to the spine's axis SA and extends from the point of sensing origin to the spine's axis SA.

As shown, in FIG. 4, the fiducial markers 154 have shifted under gravity. When the system 100 is imaged at different angles, the fiducial markers 154 of the gravity indicator (i.e., second fiducial marker component 150) are also captured. In the image, the fiducial markers 154 of the gravity indicator (i.e., second fiducial marker component 150) may be in-line with the fiducial marker of the distance locator 160.

Figure 5:
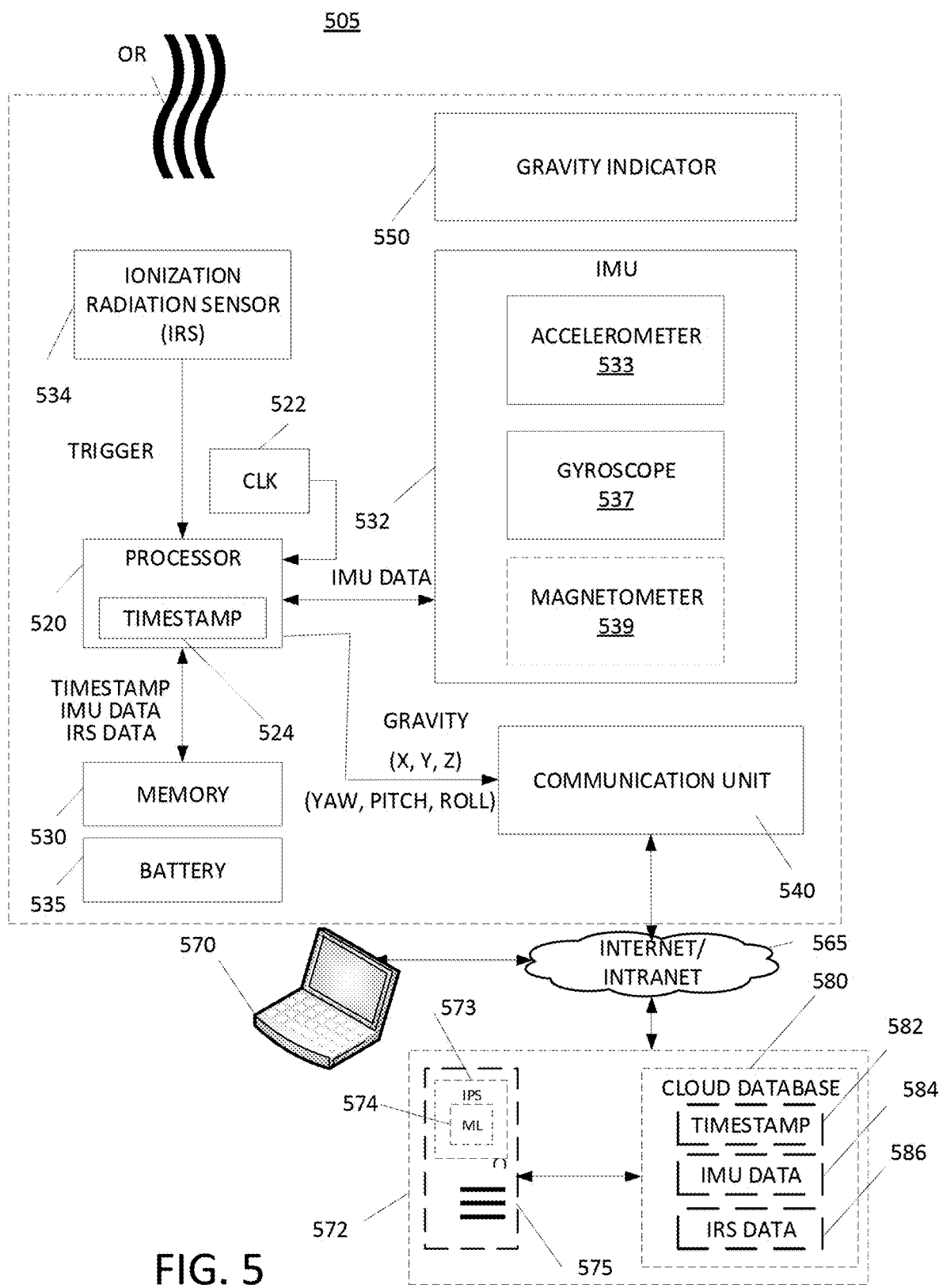
FIG. 5 is a block diagram of example electrical components of the wearable sensor device.

FIG. 5 is a block diagram of example electrical components of the wearable sensor device 505 (i.e., wearable sensor device 105). The wearable sensor device 505 may include a processor 520 and memory 530. The wearable sensor device 505 may include a clock (CLK) 522 electrically coupled to or integrated in the processor 520. The clock signal from the clock 522 may be used in generating a timestamp 524. The wearable sensor device 505 may include a battery 535 for powering the electrical components. The wearable sensor device 505 may include an IMU 532 having an accelerometer 533 and a gyroscope 537, by way of non-limiting example, or other motion sensing devices. The IMU 532 may include a magnetometer 539 represented in a dashed box to denote that it is optional. The IMU 532 (i.e., IMU 132) may be configured to detect six (6) to nine (9) degrees of freedom or human anatomy axes of motion. The device 505 may include a gravity indicator 550 (i.e., second fiducial marker component 150).

In operation, the processor 520 stores the IMU data with the timestamp 524 generated in response to the trigger from the ionization radiation sensor 534.

The wearable sensor device 505 may include a communication unit 540 configured to generate an electronic communication signal including the IMU data and a timestamp 524. The timestamp 524 generated during the baseline collection of sensed data is generated in response to the ionizing radiation sensor 534 detecting ionizing radiation (IR) from a source of ionizing radiation, such as an imaging machine 410. The stored timestamp and IMU data is also generated and collected during a monitoring phase and communicated via the communication unit 540 to a remote computing system 575 or a local computing system 570 via the Internet, Intranet or other communication network 565. The IMU data may include (X, Y, Z) Cartesian coordinates and (yaw, pitch, roll) data. The IMU data may include information associated with gravity.

The remote computing system 575 may be a website or cloud computing system 572 including a cloud database 580. The cloud database 580 stores the data including the timestamp 582, the IMU data 584 and the Ionization Radiation Sensor (IRS) data 586. The IRS data 586 synchronizes the IMU data and timestamp data collected for each instantiation of imaging at which ionizing radiation is generated. The remote computing system 575 may include an image processing system (IPS) 573 with machine learning (ML) algorithms 574 for performing one or more blocks of the methods described herein. The local computing system 570 may also include an IPS and ML algorithms for performing one or more blocks of the methods described herein.

Figure 6A:
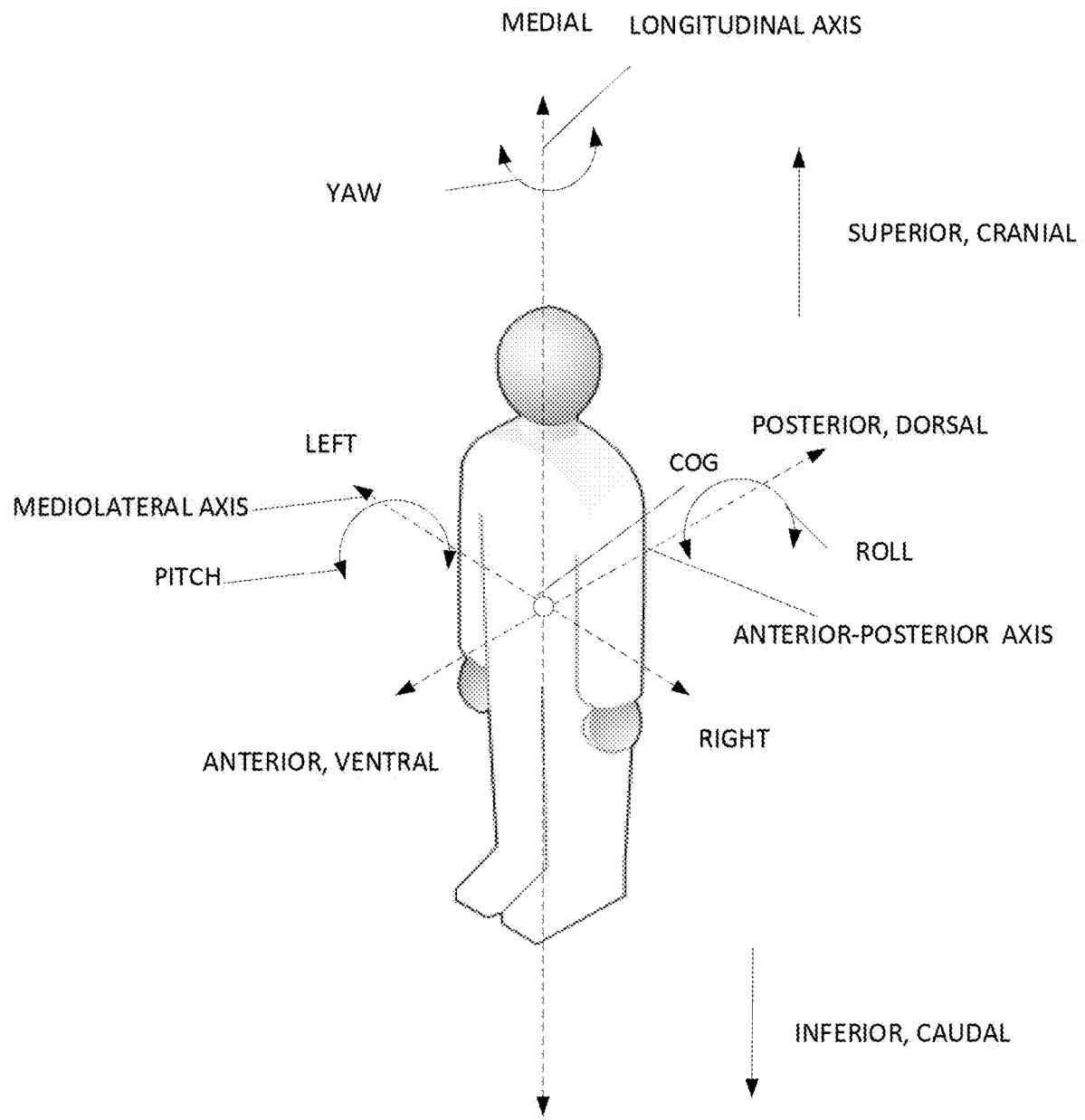
FIG. 6A is a diagram of axes of the human anatomy.
Figure 6B:
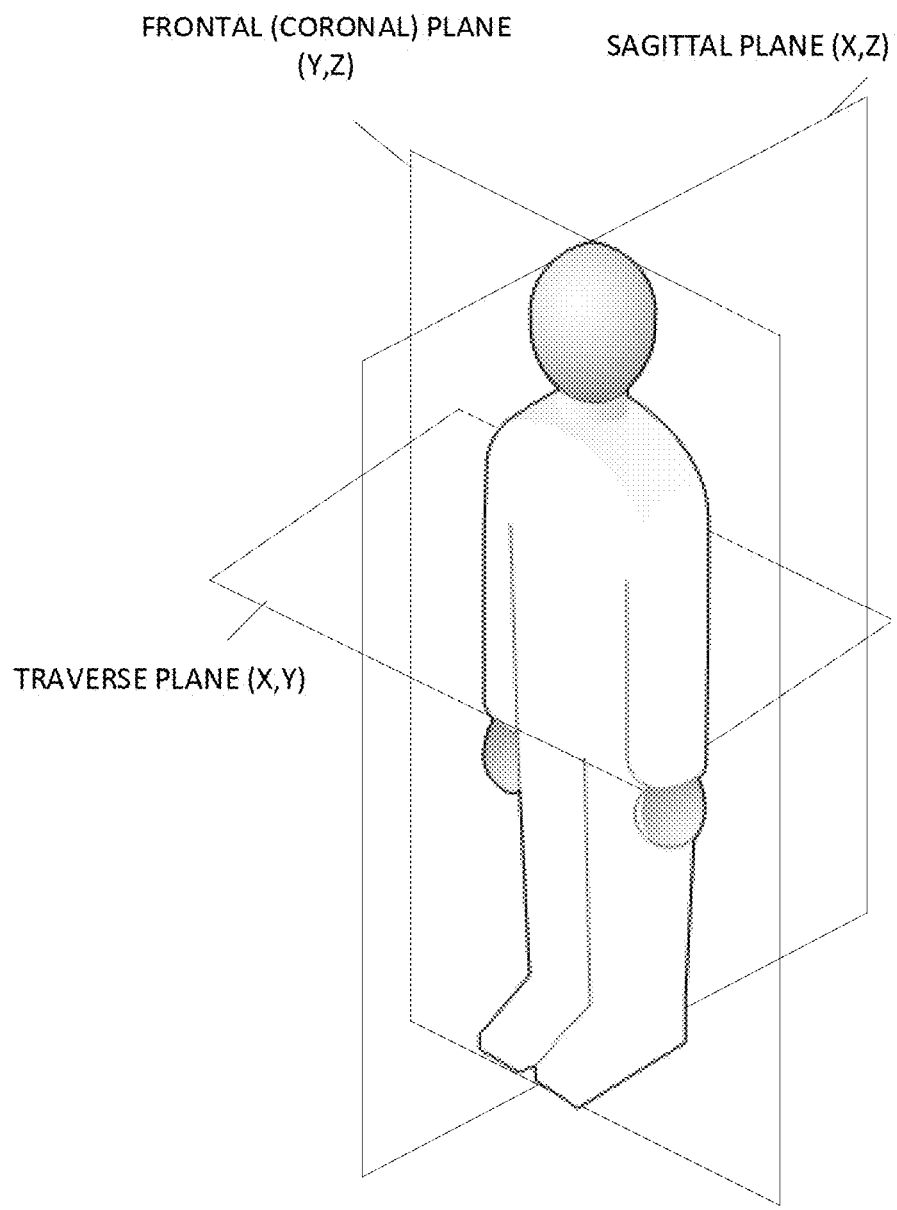
FIG. 6B is a diagram of the planes of the human anatomy.

FIG. 6A is a diagram of axes of the human anatomy 600A. FIG. 6B is a diagram of the planes of the human anatomy 600B. The sensor device 105 may be constructed and arranged as a six (6) or nine (9) axis inertial measurement unit (IMU). For example, the six degrees of freedom include (X, Y, Z) Cartesian coordinates corresponding to an X-axis, Y-axis and Z-axis. The six degrees of freedom may include information associated with the sagittal plane, frontal plane and traverse planes. Information associated with the axes may include the pitch, yaw and roll data.

The movement of the patient may include movement associated with a frontal coronal plane, a sagittal plane and/or a traverse plane.

The blocks of the methods described herein may be performed in the order shown or a different order. The one or more of the blocks may be performed contemporaneously. Method blocks may be omitted and/or added.

Figure 7:
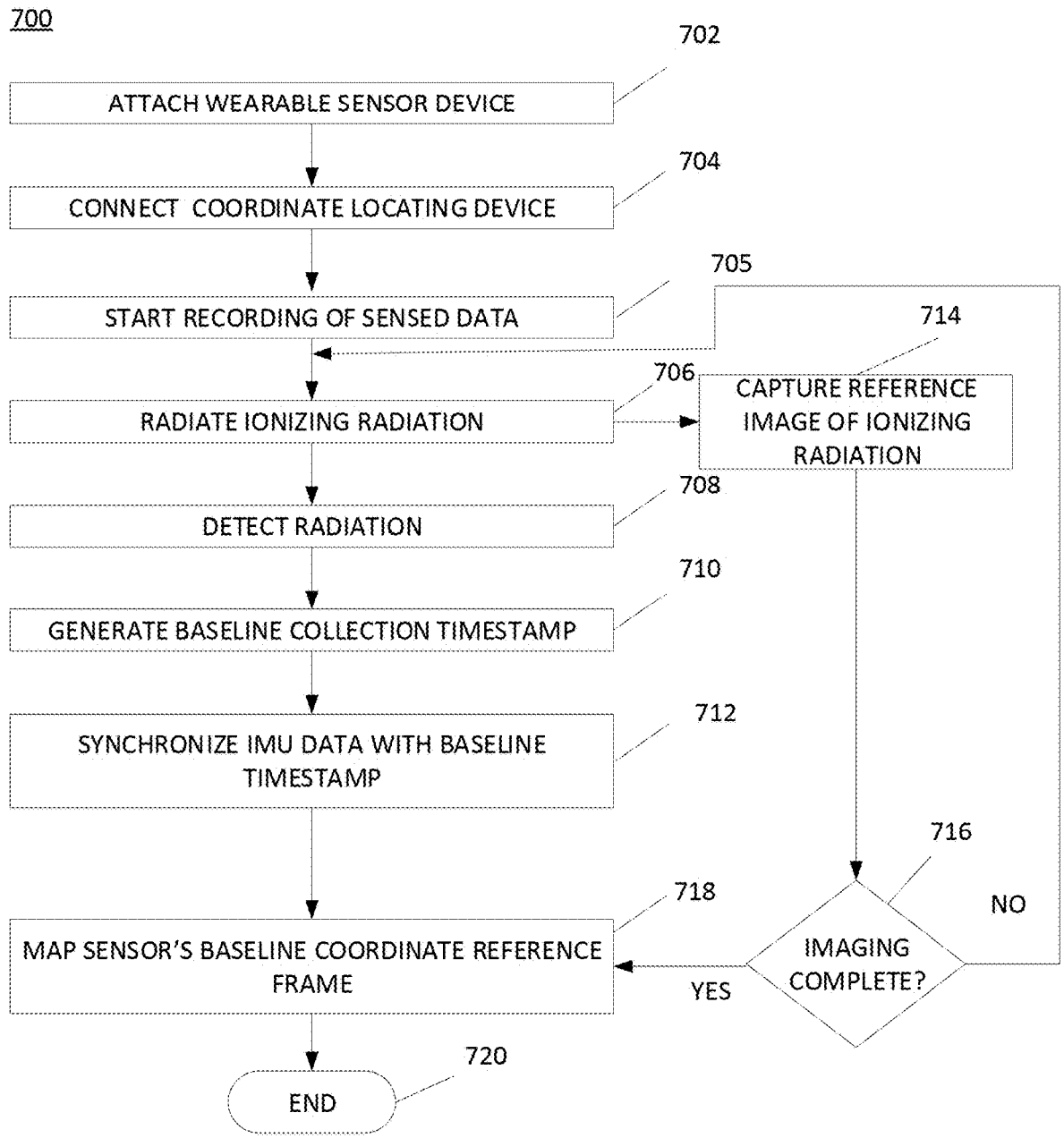
FIG. 7 is a flowchart of an embodiment method for generating a map of a sensor's baseline coordinate reference frame.

FIG. 7 is a flowchart of an embodiment of a method 700 for generating a map of a sensor's baseline coordinate reference frame. The method 700 will be described in combination with the electrical components of the sensor device 505 (i.e., sensor device 105). In operation, the method 700 may include, at block 702, affixing or attaching the wearable sensor device 105 on and to the skin 15 of a patient at a location adjacent to the thoracolumbar or trunk, via the skin-contacting interface 115. The thoracolumbar spine that may include the vertebrae T1-T12 and the intervertebral discs therebetween. The embodiments have application to the cervical section of the spine and the lumbar section of the spine. Anatomic regions of interest may include lumbar spine, pelvis, hip joint, and others. Therefore, the wearable sensor device 105 may be attached to any of these regions of interest. The method 700 may be repeated if multiple sensor device 105 are attached. Furthermore, prior to capturing the data for the baseline coordinate reference, the sensor device 105 may have already been affixed or attached.

The method 700 may include, at block 704, connecting the coordinate locating device 135 (FIG. 1) with the different fiducial marker components 140, 160 and 150 to the housing 110 of the sensor device 105 (i.e., sensor device 505).

The method 700 may include, at block 705, recording of the sensed data from the IMU 532 of the sensor device 105, once the sensor device 105 is activated. The IMU data from the IMU 532 may include accelerometer data from accelerometer 533, gyroscope data from gyroscope 537 and, in some embodiments, magnetometer data from magnetometer 539. The recording may begin prior to block 704 and may be a function of when the sensor device 105 is activated.

To generate the baseline coordinate reference, imaging should commence. The method 700 may include, at block 706, radiating ionizing radiation from an imaging machine 410 (FIG. 4). The method 700 may include, at block 708, detecting the ionizing radiation by the ionization radiation sensor 534 of the sensor device 505. The method 700 may include, at block 710, generating a baseline timestamp in response to detecting the ionizing radiation from the imaging machine 410. The method 700 may include, at block 712, synchronizing the IMU data from the IMU 132 with the baseline timestamp. The timestamp represents, in general, the instant that the radiograph was taken. The processor 520 is configured to synchronize the instantiation of imaging by the imaging machine (i.e., imaging machine 410) with the output of the IMU 532 of the wearable device 505. By way of non-limiting example, the synchronization is between an ionizing radiation sensor 534 on the wearable device 505 and the IMU 532. The ionizing radiation sensor 534 would sense the X-ray and alert the processor 520. The processor 520 would record the time using an internal clock 522 common to the IMU 532 for synchronization with the timing of the X-ray.

Synchronization between the ionizing radiation sensor 534 and the IMU 532 of the wearable device 505 may use signals received via communication unit 540. For example, the imaging machine 410 or another device could send a signal to the wearable device 505 corresponding to the moment of the radiation of the ionizing radiation (OR) from an imaging machine. By way of non-limiting example, the IMU data may include (X, Y, Z) Cartesian coordinates and (yaw, pitch, roll) data. The IMU data may include information associated with gravity.

The method 700 may include, at block 714, capturing by the imaging machine 410 images, in response to radiating the patient with the ionizing radiation. The images can be a single image in which the patient is still, or a series of images in which the patient moves their trunk using their boney anatomy structures 405 (FIG. 4). The method 700 may include, at block 716, a determination whether imaging is complete. If the determination is "NO," the method loops back to block 706 where capturing of images continues. If the determination is "YES," the method 700 may include, at block 718, mapping a sensor's baseline coordinate reference frame based on the synchronized IMU data and the captured images. In the captured images, the different fiducial marker(s) of the coordinate locating device 135 are captured along with the IMU 532 and underlying boney anatomy structure 405 to identify a landmark 407. Each marker is registered to a set of pixels in the captured image corresponding to the marker's pixel location in the image. The mapping at block 718 may be performed by a remote computing system 575 or a local computing system 570. A different baseline coordinate reference frame may be generated for a different landmark identified on the underlying boney anatomy structure 405.

The coordinate locating device 135 may include markers 141, 142 and 143. When imaging is performed, the coordinate locating device 135 is imaged from different angles or pose. A 3D representation of the fiducial markers 141, 142 and 143 may be used to develop a baseline of the sensor data in a 2D representation of the image. The radiopaque markers 141, 142 and 143 allows the device's position and orientation within an image to be matched to a pixel coordinate system of the imaging machine 410. The fiducial marker 160 of the position locator provides a calibration length in the image. The calibration length is associated with pixels in the image that correspond to the length.

The coordinate locating device 135 may further include radiopaque gravity direction markers 154 that may be imaged simultaneously when fiducial markers 141, 142 and 143 and fiducial marker 160 are imaged. Each image from the imaging machine 410 causes the ionization radiation sensor 534 to trigger a timestamp for synchronizing the IMU data reading with the instantiation of imaging. The IMU data may include data representative of the gravity reading of the IMU 532 that is paired with the baseline timestamp. Thus, the image processing analysis via the IPS 573 is configured to compare the gravity reading of the IMU 532 with the direction of gravity vector imaged processed gravity reading based on the position of fiducial markers 154 to compensate for any offsets in the IMU gravity. The processor 520 configured to synchronize an internal clock 522 used by the IMU with the baseline timestamp. The clock 522 being adjusted based on the logged time of the baseline timestamp. The IMU data being adjusted based on a baseline anatomical position logged at the time of the baseline timestamp. The sample rate of the IMU 532 may be constant, in some embodiments.

Once the mapping is complete, one or more of the sensors' baseline coordinate reference frames have been generated and the method 700 ends, at block 720. By way of non-limiting example, different landmarks may be used to generate different baseline coordinate reference frames.

Figure 8:
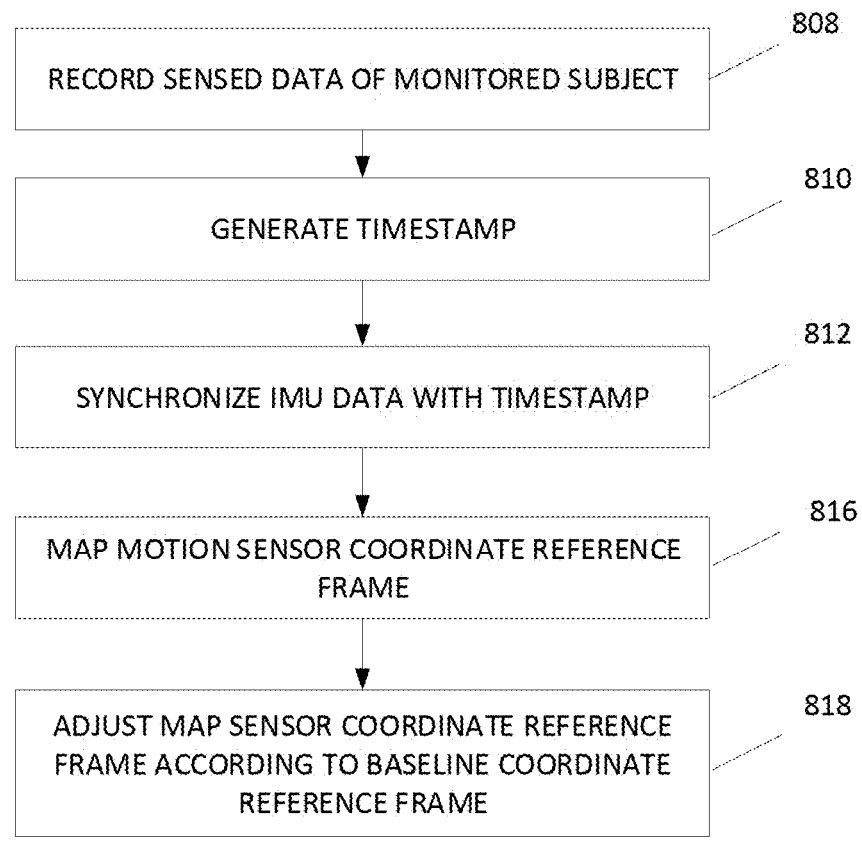
FIG. 8 is a flowchart of an embodiment method for generating a map of a motion sensor coordinate reference frame.

FIG. 8 is a flowchart of an embodiment of a method for generating a map of a motion sensor coordinate reference frame. The method 800 may include, at block 808, recording of the sensed data from the IMU 532 of the sensor device 505. The recording of data in the method 800 is the monitored data after the baseline coordinate reference frame has been generated. The recording may take place over several days, for example.

The IMU data from the IMU 532 may include accelerometer data from accelerometer 533, gyroscope data from gyroscope 537 and, in some embodiments, magnetometer data from magnetometer 539.

The method 800 may include, at block 810, generating a timestamp using the internal clock 522. The method 800 may include, at block 812, synchronizing the IMU data from the IMU 532 with the timestamp of the clock 522. By way of non-limiting example, the IMU data may include (X, Y, Z) Cartesian coordinates and (yaw, pitch, roll) data. The IMU data may include information associated with gravity. The method 800 may include, at block 816, mapping the sensor's coordinate reference frame based on the motion sensed data. The method 800 may include, at block 818, adjusting the map motion sensor coordinate reference frame according to an offset with the baseline coordinate reference frame.

Figure 9A:
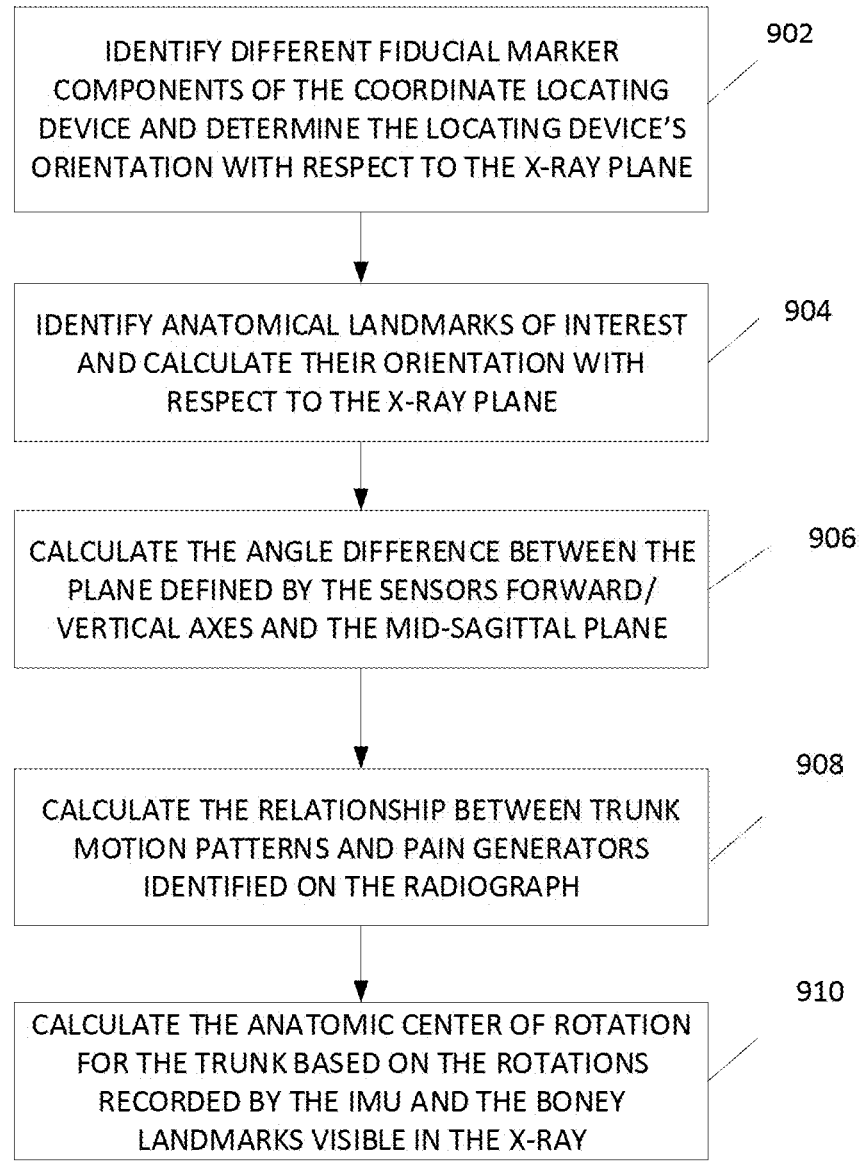
FIG. 9A is a flowchart of an embodiment method for analyzing the map of the sensor's baseline coordinate reference frame.
Figure 9B:
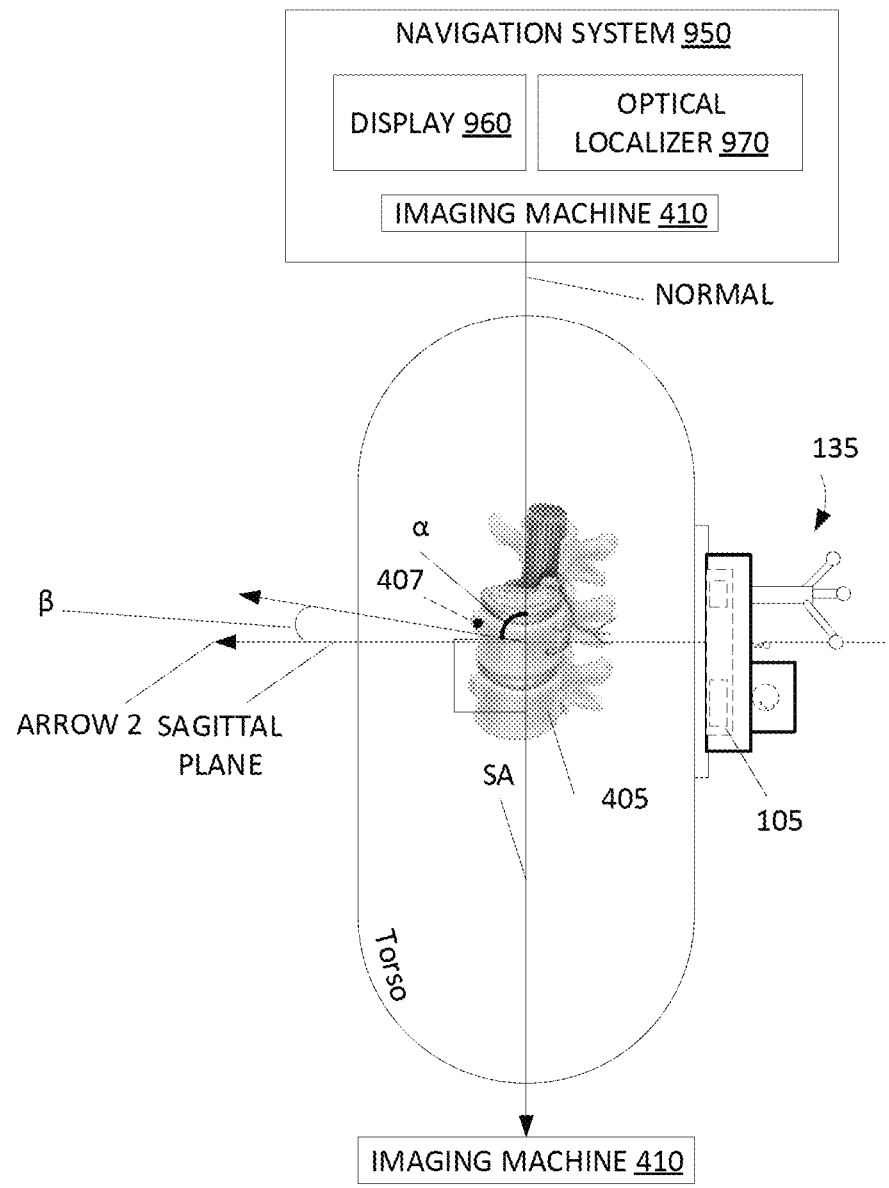
FIG. 9B is a diagram of an example sagittal plane offset.

FIG. 9A is a flowchart of an embodiment of a method 900 for analyzing the map of the sensor's baseline coordinate reference frame. FIG. 9B is a diagram of an example sagittal plane offset. The method 900 may include, at block 902, identifying different fiducial marker components of the coordinate locating device 135 and determine orientation of the different fiducial marker components with respect to the X-ray plane or imaging machine's plane, as will be described in more detail in relation to FIGS. 10-11.

Embodiments of the imaging devices herein may relate generally, for example, to systems, devices, and methods for image guided medical procedures. More particularly, embodiments of the imaging device may relate to surgical navigation systems 950, devices, and methods with anatomical tracking for performing image guided medical procedures. For example, such surgical navigation systems 950, devices, and methods may be those used in the FluoroNav™ system that utilizes the StealthStation® Treatment Guidance Platform, both of which are available from Medtronic Sofamor Danek, Inc. The StealthStation® Treatment Guidance Platform, and in particular the StealthStation® Navigation System, is described in part in the "StealthStation® S7® Treatment Guidance System Manual" published by Medtronic, Inc. in 2012, the "StealthStation™ S8 Spinal Navigation Solution" brochure published by Medtronic, Inc. in 2019, and in "The Clinical and Economic Benefits of Using StealthStation® Navigation and O-arm® Imaging Systems for Spine Surgery" brochure published by Medtronic, Inc. in 2014. Embodiments of the surgical navigation systems 950, devices, and methods with anatomical tracking, as shown in FIG. 9B.

The imaging machine 410 may be part of a StealthStation® Navigational System such as a StealStation® S7® or StealStation® S8® by Medtronic Inc. The navigation system 950 may include a display 960. The navigation system 950 being configured to create a translation map between all or a subset of points in the patient image and corresponding points on the patient anatomy. The imaging machine 410 is configured to provide registration and image acquisition for navigation. The imaging machine may provide optical systems to determine the position of the (optical) markers. The imaging machine may include an optical localizer 970. The optical localizer 970 may include a camera with a field of view that defines an optical navigation field by detecting optical markers and determines their spatial positions using triangulation in a displayed image. The optical localizer 970 may include a laser positioning system associated with the camera.

While, the embodiments describe passive optical radiopaque fiducial markers, one or more of the fiducial markers may include a light emitting diode (LED). In such an embodiments, the coordinate locating device would be equipped with a battery or power source (not shown).

The imaging machine 410 may be an O-arm® Imaging System, by Medtronic Inc., configured to provide high-resolution real-time 2D fluoroscopic and 3D imaging with multiplanar view.

In one or more cases, the navigation system 950 may be configured to register the acquired image data to one or more coordinate systems. In one or more cases, one or more smartglasses (not shown) are configured to display one or more superimposed images over a portion of the patient. In one or more cases, the one or more superimposed images may be related to the acquired image data. In one or more cases, the one or more smartglasses are further configured to align the one or more superimposed images to correspond with a position of the at least one object.

In some embodiments, the imaging device may include those disclosed in U.S. Pat. Nos. 7,188,998; 7,108,421; 7,106,825; 7,001,045; and 6,940,941; all of which are incorporated herein in their entirety by reference, or any appropriate portions thereof.

The method 900 may include, at block 904, identifying anatomical landmarks 407 (FIG. 4) of interest and calculate their (i.e., landmarks) orientation with respect to the X-ray plane or imaging machine's plane. Assume, that the spine's axis (SA) is normal or orthogonal to the X-ray plane or imaging machine's plane. By way of non-limited example, calculate the angle (u) between the mid-sagittal plane and the X-ray plane using existing methods.

There are three sets of planes, X-ray plane, anatomic planes and sensor planes. For example, for an X-ray plane, a single plane is fixed relative to the imaging machine. The anatomic planes may include three orthogonal planes (sagittal, coronal, and axial) that are fixed with respect to the person. The sensor planes may include three planes (X-Y, Y-Z, and X-Z) that are fixed relative to the sensor of the sensor device 105. The anatomic planes may be misaligned with the X-ray plane. The amount of misalignment (i.e., out-of-plane angle) would be calculated using the methods described herein, for example, as related to FIGS. 9A-9B, 10, 11 and 12.

For example, in block 906, the sensor planes may be misaligned with the anatomic planes. The amount of misalignment would be determined by i.) identify misalignment between the midsagittal plane and the X-ray plane using the existing methods; ii.) identify the misalignment between the sensor plane and the X-ray plane by using the locations of fiducial markers 141, 142, and 143; and iii.) subtract the misalignment calculated in (i.) from the misalignment calculated in (ii.).

The method 900 may include, at block 906, calculating the angle ($\beta$) being the difference between the plane defined by the sensors forward/vertical axes and the mid-sagittal plane in the direction of ARROW 2. By way of non-limiting example, all of the IMU data may be rotated by this angle ($\beta$) so that the sensor's baseline coordinate reference frame is aligned to the mid-sagittal plane.

The method 900 may include, at block 908, calculating the relationship between trunk motion patterns and pain generators identified on the radiograph such as using the X-ray machine or CT scan machine.

The method 900 may include, at block 910, calculating the anatomic center of rotation for the trunk based on the rotations recorded by the IMU 132 and the boney landmarks 407 visible in the captured image by the imaging machine.

The coordinate locating device 135 with radiopaque fiducial markers are affixed to the sensor device 104 while the sensor device 105 is being worn by an individual. In some scenarios, the patient will be standing upright. Then, the spine of the patient and the device 105 are imaged with ionizing radiation in one or more planes. Multiple images may be captured in succession to show the fiducial markers for calculating the distance between the markers and the sensing axes of the baseline coordinate reference frame. The distance between the baseline coordinate reference frame and relevant boney landmarks can then be determined.

Figure 10:
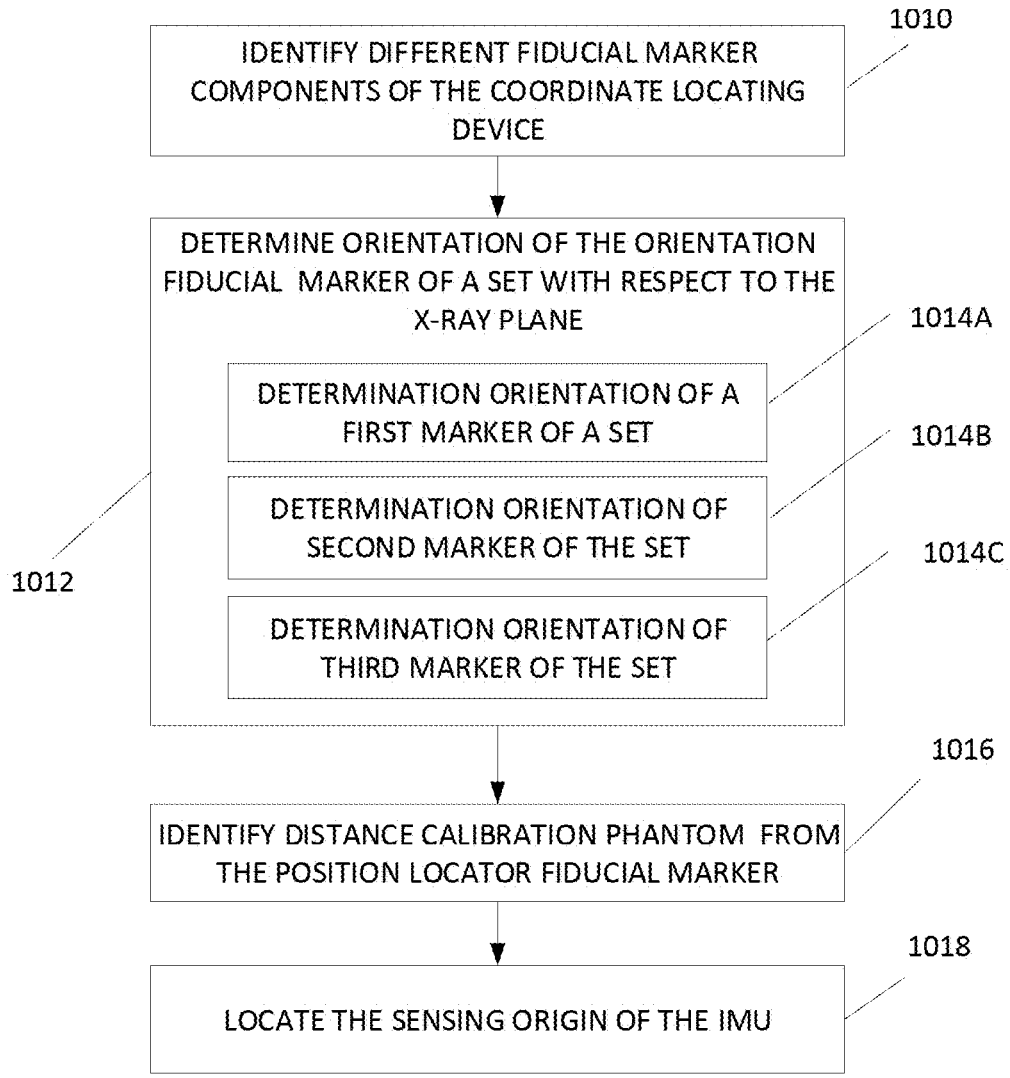
FIG. 10 is a flow chart of an embodiment method for identifying fiducial marker components of a coordinate locating device and the orientation relative to the X-ray plane to locate the point of sensing origin of an inertial measurement unit (IMU).

FIG. 10 is a flowchart of an embodiment of a method 1000 for identifying the different fiducial marker components of the coordinate locating device 135 and their orientation relative to the X-ray plane to locate the point of sensing origin of the inertial measurement unit (IMU). FIG. 10 will be described in relation to FIG. 9B. The method 1000 corresponds to the functions to be performed at block 902 of the method 900.

The method 1000 may include (at step 1010) identifying fiducial markers 141, 142, and 143 for 3D space representation in a 2D image, identifying the distance locator fiducial marker 160 and notch 164 in the image; and identifying the at least one gravity direction fiducial marker 154 in the image. The image may be processed using image processing analysis via the IPS 573 to perform feature extraction using machine learning algorithms and/or deep learning algorithms including supervised and unsupervised learning algorithms. The feature extraction and classification algorithms such as for identifying landmarks of the boney structures may be used.

The method 1000 may include determining the orientation of the fiducial marker components with respect to the X-ray plane or the imaging machine's plane (FIG. 9B), at block 1012. At block 1012, the method 1000 may determine the position of marker 141 at block 1014A, marker 142 at block 1014B, and marker 143, at block 1014C. There are known algorithms to determine the out-of-plane rotation of 3D space fiducial markers arranged in a non-collinear orientation.

The method 1000 may include, at block 1016, identifying a distance calibration phantom via the distance locator fiducial marker 160, as will be described in more detail in relation to FIG. 12. The method 1000, may include (at step 1018) locating the point of sensing origin of the IMU 532. The point of sensing origin is registered to set the coordinates of the point of sensing origin to X=0, Y=0 and Z=0 denoted as (0, 0, 0) in sensor's coordinate reference frame and would be calculated based on a known distance between the distance locator (i.e., the distance locator fiducial marker 160) and the sensor package, such as the chip or circuit of the IMU 132. The image processing analysis via the IPS 573 would determine a pixel length metric of a fixed length between the fiducial marker 160 and the notch 164. The image processing analysis via the IPS 573 calibrates the pixel length D1 to extrapolate the distance D2 (FIG. 4) such as to the spine's axis (SA).

The chamber 152 containing the gravity direction radiopaque fiducial markers 154 gives an indication of the direction of the gravity vector. This information can be used in two ways. First, the gravity vector may be used, for example, to inform radiographic measures, such as the C7 plumb line, that require knowledge of the gravity vector. Traditionally, radiologists/spine specialists approximate the gravity vector when drawing measurements that use it. The radiopaque fiducial markers 154 may be used as a tool to identify the gravity vector. Second, the gravity vector may ensure that the gravity vector measured by the IMU does not deviate significantly from the gravity line that will be used in radiographic measurements of the spine. The gravity vector derived from the image of the chamber 152 containing gravity direction radiopaque fiducial markers 154 may not necessarily be used to calibrate the accelerometer of the IMU. However, the gravity direction radiopaque fiducial markers 154 may, for example, be used as an in vivo measure of accuracy to determine if the accelerometer is not suitable for use. Through these two uses, the gravity direction radiopaque fiducial markers 154 serves to strengthen the connection between the anatomy and the sensor data. Both the IMU data and relevant radiographic parameters are calibrated according to a common gravity indicator.

Figure 11:
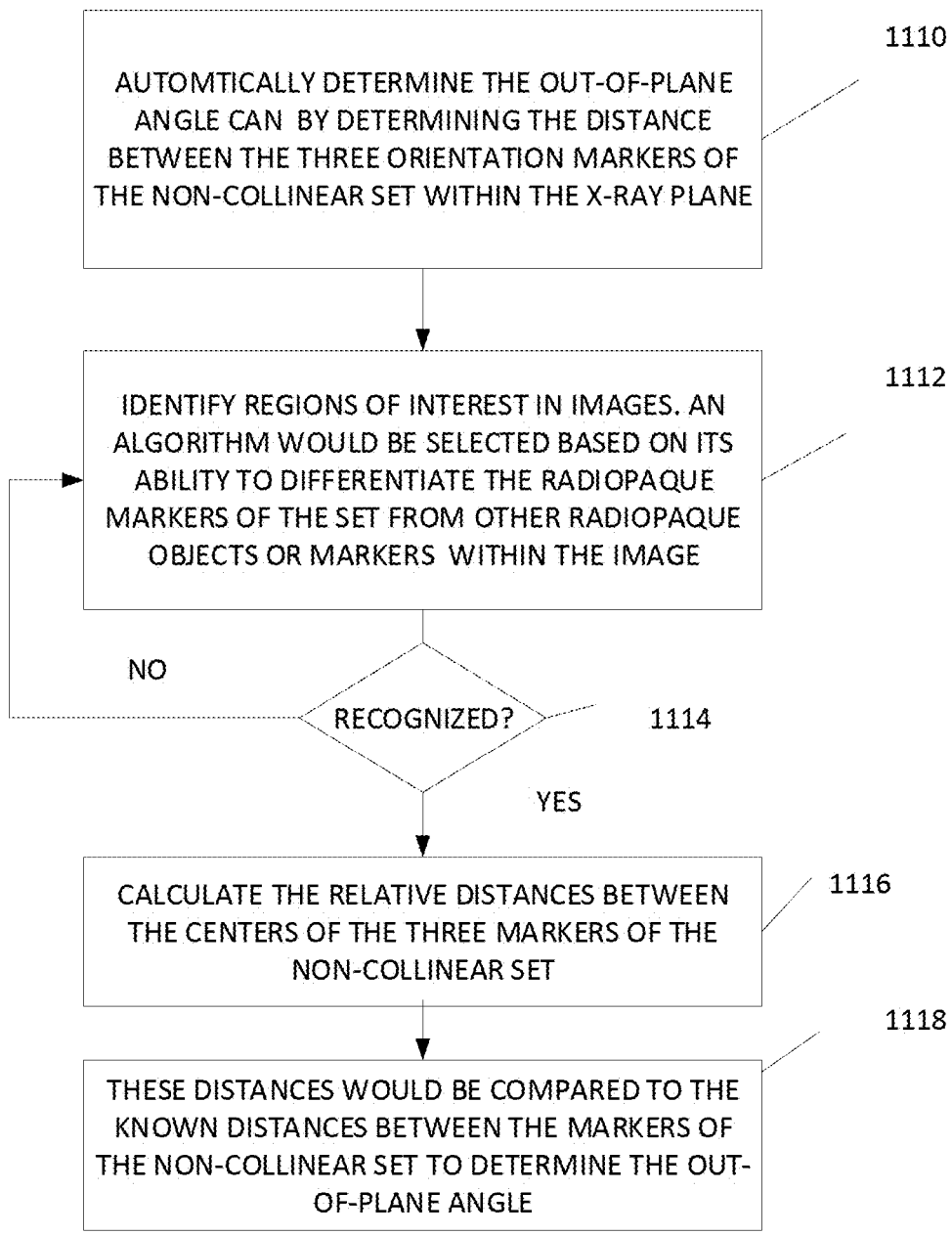
FIG. 11 is a flowchart of an embodiment method for determining an orientation of a set of non-collinear fiducial markers relative to the X-ray plane to generate a three-dimensional (3D) space pixel metric for a sensor's baseline coordinate reference frame.

FIG. 11 is a flowchart of an embodiment of a method 1100 for determining an orientation of the set of non-collinear fiducial markers relative to the X-ray plane to generate a 3D space pixel metric for the sensor's baseline coordinate reference frame. The method 1100 corresponds to the functions to be carried out at block 1012 of FIG. 10. The method 1100 may include, at block 1110, automatically determining the out-of-plane angle (i.e., angle j) by determining the distance between the three orientation fiducial markers 141, 142 and 143 within the X-ray plane.

The method 1100 may include, at block 1112, identifying regions of interest in images using machine learning (ML). An algorithm would be selected based on its ability to differentiate the radiopaque fiducial markers 141, 142, 143 from other radiopaque objects or fiducial markers within the same image. The method 1100 may include determining where each fiducial marker of the non-collinear marker set is recognized, at block 1114. If the determination is "NO," the method loops back to block 1112 until all the fiducial markers of the non-collinear set are recognized for the 3D space pixel metric. If the determination is "YES," the method, at block 1116, may include calculating the relative distances between the centers of the three markers of the non-collinear set. The method 1100 may include, at block 1118, comparing these distances to the known distances between the markers of the non-collinear set to determine the out-of-plane angle 3.

Figure 12:
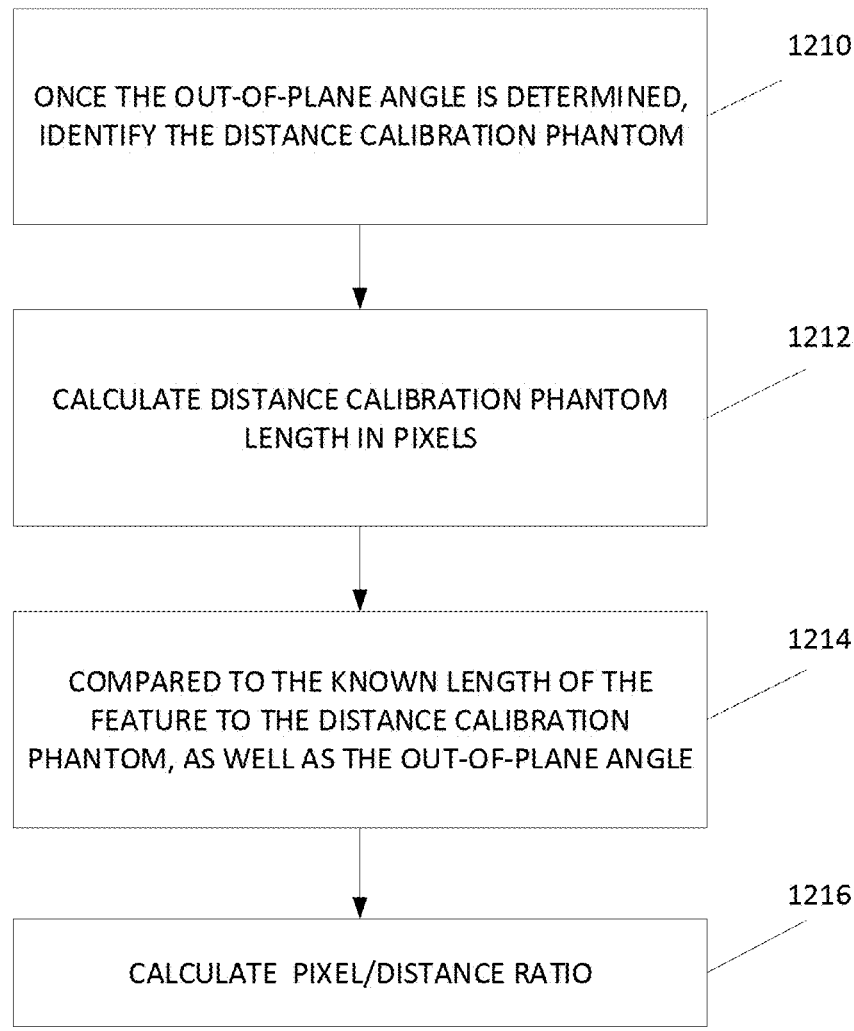
FIG. 12 is a flowchart of an embodiment method for identifying the distance calibration phantom pixel metric for the sensor's baseline coordinate reference frame.

FIG. 12 is a flowchart of an embodiment of a method 1200 for identifying the distance calibration phantom pixel metric for the sensor's baseline coordinate reference frame. The method 1200 may correspond to the functions to be carried out by block 1016 of FIG. 10.

The method 1200 may include, at block 1210, once the out-of-plane angle 3 is determined, identify the distance calibration phantom (i.e., the distance locator fiducial marker 160). The method 1200 may include, at block 1212, calculating the distance calibration phantom length in pixels to develop a calibration pixel length metric. The method 1200 may include, at block 1214, comparing the distance phantom length to the known length of the feature, as well as the out-of-plane angle 3. The method 1200 may include, at block 1216, calculating a pixel/distance ratio. This ratio can be used to calculate a distance between the sensor's point of sensing origin in Cartesian coordinate reference frame) and various parts of the spine in the image.

The thoracolumbar spine may include the vertebrae T1-T12 and the intervertebral discs therebetween.

Relevant anatomic landmarks include the posterior superior corner of the first sacral vertebra (S1), the C7 plumb line (i.e., a vertical line parallel to gravity drawn from the center of the seventh vertebra of the cervical spine to the ground), the center of the femoral head, the midpoint of the sacral plate, and other anatomical boney structures.

The images can be planar or CT. They can be single-shot images in which the individual is still, or a series of shots in which the individual moves their trunk. The distance between known points on the coordinate locating device 135 is used to determine the pixel/distance ratio. Then, the distance between the sensor's point of sensing origin in Cartesian coordinate reference frame and various parts of the spine can be calculated. The sensor device 105 in the primary embodiment would be a 6- or 9-axis inertial measurement unit. Relevant anatomic landmarks include the posterior superior corner of S1, the C7 plumb line, the center of the femoral head, the midpoint of the sacral plate, and many more.

The system 100 is configured to bridge the gap in surgeon's minds between familiar data (imaging studies of the spine) and the unfamiliar data captured through the wearable device 105 (human motion data). In the current standard practice for the treatment of spinal diseases, the surgeon consults imaging studies of the spine to determine the amount of surgical correction required by the patient. It is widely recognized that the posture adopted by an individual during imaging studies may not be fully representative of that individual's true comfortable posture. The human motion data captured continuously for multiple days by the wearable device can shed light on the individual's true comfortable posture.

While the embodiments provide the radiopaque fiducial markers on a coordinate locating device, the radiopaque fiducial markers may be built into the wearable sensor device 105.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described methods or one or more blocks of the methods may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 13:
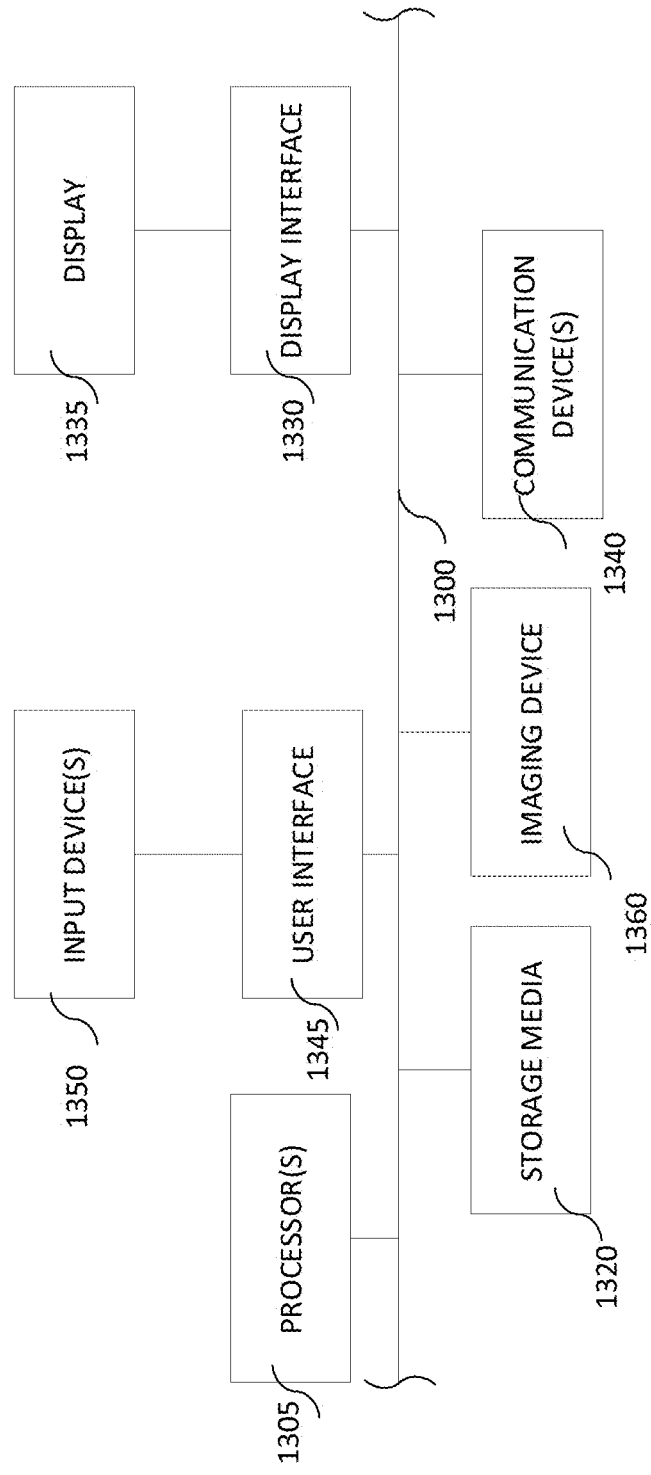
FIG. 13 depicts an example of internal hardware that may be included in any of the electronic components of an electronic device.

FIG. 13 depicts an example of internal hardware that may be included in any of the electronic components of an electronic device as described in this disclosure such as, for example, an on-premises electronic device, an associate electronic device, a remote electronic device, remote computing system, local computing system and/or any other integrated system and/or hardware that may be used to contain or implement program instructions. The wearable sensor device 105 is an electronic device.

A bus 1300 serves as the main information highway interconnecting the other illustrated components of the hardware. CPU 1305 is the central processing unit of the system, performing calculations and logic operations required to execute a program. CPU 1305, alone or in conjunction with one or more of the other elements disclosed in FIG. 13, is an example of a processor as such term is used within this disclosure. Read only memory (ROM) and random access memory (RAM) constitute examples of tangible and non-transitory computer-readable storage media 1320, memory devices or data stores as such terms are used within this disclosure. The memory device may store an operating system (OS) of the server or for the platform of the electronic device.

Program instructions, software or interactive modules for providing the interface and performing any querying or analysis associated with one or more data sets may be stored in the computer-readable storage media 1320. Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 1330 may permit information from the bus 1300 to be displayed on the display 1335 in audio, visual, graphic or alphanumeric format. Communication with external devices may occur using various communication devices or ports 1340. A communication devices or ports 1340 may be attached to a communications network, such as the Internet or an intranet. In various embodiments, communication with external devices may occur via one or more short range communication protocols. The communication devices or ports 1340 may include communication devices for wired or wireless communications.

The hardware may also include an interface 1345, such as graphical user interface (GUI) that allows for receipt of data from input devices such as a keyboard or other input device 1350 such as a mouse, a joystick, a touch screen, a remote control, a pointing device, a video input device and/or an audio input device. The interface 1345 may include a sensor, such as without limitations, in touch screens. The hardware may include imaging device 1360 configured to capture images using ionizing radiation. The imaging device 1360 is an ionizing radiation machine.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge from which a computer can read. The term non-transitory computer-readable storage medium is used herein to refer to any medium that participates in providing information to processor, except for carrier waves and other signals.

Computer program code for carrying out operations described above may be written in a variety of programming languages, including but not limited to a high-level programming language, such as without limitation, C or C++, Python, and Java for development convenience. In addition, computer program code for carrying out operations of embodiments described herein may also be written in other programming languages, such as, but not limited to, interpreted languages. The program code may include hardware description language (HDL) or very high speed integrated circuit (VHSIC) hardware description language, such as for firmware programming. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM and a flash memory. Otherwise, the code can be stored in a non-transitory, tangible computer-readable storage medium such as a magnetic tape, a flexible disc, a hard disc, a compact disc, a photo-magnetic disc, a digital versatile disc (DVD) or the like.

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A wearable sensor device comprising:
   a housing configured to be attached to a region of a body of a subject;
   an inertial measurement unit (IMU) within the housing configured to, when the housing is attached to the subject, sense motion of the subject;
   an x-ray sensor disposed within the housing, the x-ray sensor configured to generate a trigger in response to sensing x-rays, the housing configured to allow x-rays from an x-ray imaging system outside the housing to trigger the x-ray sensor;
   a memory within the housing;
   a processor within the housing and configured to, during a period of time the wearable sensor device is worn by the subject:
      receive data from the IMU and store the data in the memory; and
      in response to receiving the trigger from the x-ray sensor, store a timestamp in the memory; and
   a communication unit within the housing and configured to transmit the stored data and the stored timestamp to a computing system using a communication network,
   wherein the housing of the wearable sensor device is further configured to receive a removeable coordinate locating device comprising a plurality of radiopaque fiducial elements, the plurality of radiopaque fiducial elements configured to indicate a coordinate frame of the IMU based on a location of the IMU within the housing and a position of the removeable coordinate locating device when the removeable coordinate locating device is received by the housing.

2. The wearable sensor device of claim 1, wherein:
   the computing system is configured to store medical images of the subject; and
   the communication unit is configured to transmit the stored data and the stored timestamp to the computing system, causing the computing system to correlate one or more medical images with the stored data using the stored timestamp.

3. The wearable sensor device of claim 1, wherein the IMU comprises a magnetometer.

4. The wearable sensor device of claim 1, wherein the plurality of radiopaque fiducial elements includes elements configured to indicate a gravity direction.

5. The wearable sensor device of claim 4, wherein the elements configured to indicate the gravity direction are configured to shift position under gravity.

6. The wearable sensor device of claim 1, wherein the removeable coordinate locating device comprises a support structure configured to connect to the housing of the wearable sensor device such that the support structure has a known orientation and location with respect to the housing.

7. The wearable sensor device of claim 6, wherein the housing is dimensioned to receive the support structure.

8. The wearable sensor device of claim 6, wherein the support structure is configured to slide onto the housing of the wearable sensor device.

9. The wearable sensor device of claim 6, wherein the plurality of radiopaque fiducial elements are connected to the support structure.

10. The wearable sensor device of claim 1, wherein the x-ray sensor comprises a circuit board with an x-ray sensitive element coupled thereto, the x-ray sensor configured to signal the processor at a moment in time that the x-ray sensor senses the x-rays.

11. The wearable sensor device of claim 10, wherein the x-ray sensor does not generate an image.

12. The wearable sensor device of claim 1, wherein the removeable coordinate locating device has dimensions relative to the housing to facilitate receiving the removeable coordinate locating device and fix the position of the removeable coordinate locating device with respect to the coordinate frame of the IMU.

13. The wearable sensor device of claim 1, wherein the processor is configured to store the timestamp in the memory by recording, at a moment in time of receiving the trigger from the x-ray sensor, a timestamp from a clock that is electrically coupled to or integrated within the processor.

* * * * *